US012714409B2

(12) United States Patent
Soma et al.

(10) Patent No.: US 12,714,409 B2
(45) Date of Patent: Aug. 25, 2026

(54) COMPRESSION DEVICE

(71) Applicant: TERUMO KABUSHIKI KAISHA, Tokyo (JP)

(72) Inventors: Yuki Soma, Campbell, CA (US); Masakatsu Kawaura, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 353 days.

(21) Appl. No.: 18/363,157

(22) Filed: Aug. 1, 2023

(65) Prior Publication Data

US 2023/0371939 A1 Nov. 23, 2023

Related U.S. Application Data

(63) Continuation of application No. PCT/JP2022/010145, filed on Mar. 8, 2022.

(30) Foreign Application Priority Data

Mar. 17, 2021 (JP) ................................ 2021-044070

(51) Int. Cl.
*A61B 17/00* (2006.01)
*A61B 17/12* (2006.01)

(52) U.S. Cl.
CPC .................... *A61B 17/0057* (2013.01); *A61B 2017/00557* (2013.01); *A61B 2017/12004* (2013.01)

(58) Field of Classification Search
CPC ... A61B 17/0057; A61B 17/12; A61B 17/132; A61B 17/1325; A61B 17/135;

(Continued)

(56) References Cited

U.S. PATENT DOCUMENTS 3,454,010 A * 7/1969 Clifton ...................... A61F 5/34 601/149
4,224,945 A * 9/1980 Cohen ............... A61F 13/00063 602/53

(Continued)

FOREIGN PATENT DOCUMENTS

| | | | |
|---|---|---|---|
| JP | 2005521464 | A | 7/2005 |
| WO | 2016163326 | A1 | 10/2016 |
| WO | 2018181314 | A1 | 10/2018 |

OTHER PUBLICATIONS

English Translations of the International Search Report (Form PCT/ISA/210) and the Written Opinion of the International Searching Authority (Form PCT/ISA/237) issued May 31, 2022, by the Japan Patent Office in corresponding International Application No. PCT/JP2022/010145. (6 pages).

(Continued)

*Primary Examiner* — Dianne Dornbusch
(74) *Attorney, Agent, or Firm* — Buchanan Ingersoll & Rooney PC

(57) ABSTRACT

A compression device includes: an adhesion surface configured to be adhered to a biological surface; and an inflatable portion configured to compress the biological surface. The inflatable portion defines an accommodation space capable of accommodating a fluid, and the inflatable portion is capable of being inflated in a thickness direction from a flat deflated form and being changed to an inflated form by supplying the fluid to the accommodation space. The inflatable portion is provided with an inflation restricting portion that is provided at a position sandwiched or surrounded by inflation regions inflatable in the thickness direction in a plan view viewed along the thickness direction, and in which inflation in the thickness direction is restricted by the inflation regions.

15 Claims, 18 Drawing Sheets

(58) Field of Classification Search

CPC . A61B 2017/00557; A61B 2017/12004; A61F 5/30; A61F 5/32; A61F 5/34; A61F 13/02; A61F 13/0203; A61F 2013/0028; A61F 2013/00089; A61F 2013/00463; A61F 2013/00468

See application file for complete search history.

(56) References Cited

U.S. PATENT DOCUMENTS 5,527,264 A * 6/1996 Moll .................... A61B 90/50 600/207
5,643,315 A 7/1997 Daneshvar
5,865,728 A * 2/1999 Moll .................... A61B 90/50 600/207
6,066,154 A * 5/2000 Reiley ................. A61B 10/025 606/94
7,544,213 B2 * 6/2009 Adams ................. A61F 2/0063 623/23.72
2003/0229372 A1 * 12/2003 Reiley .................. A61F 2/4601 606/192
2012/0029406 A1 2/2012 Bates et al.
2018/0028195 A1 * 2/2018 Benz ................... A61B 17/135
2018/0042615 A1 2/2018 Kimura et al.
2019/0029693 A1 1/2019 Okamura
2021/0204953 A1 * 7/2021 Kawaura ........... A61B 17/0057

OTHER PUBLICATIONS

International Search Report (PCT/ISA/210) with translation and Written Opinion (PCT/ISA/237) mailed on May 31, 2022, by the Japan Patent Office as the International Searching Authority for International Application No. PCT/JP2022/010145. (8pages).

* cited by examiner 1
28
2b
2a
7(3)
10b(6b)
7b
II
II
13a
(7a)
6c
10a
(6a)
6(3)
4(2)
A2(A)
C2
(C)
B
A1(A)
C1
(C)

COMPRESSION DEVICE

CROSS-REFERENCES TO RELATED APPLICATIONS

This application is a continuation of International Application No. PCT/JP2022/010145 filed on Mar. 8, 2022, which claims priority to Japanese Application No. 2021-044070 filed on Mar. 17, 2021, the entire content of both of which is incorporated herein by reference.

TECHNOLOGICAL FIELD

This disclosure relates to a compression device.

BACKGROUND DISCUSSION

In recent years, in medical institutions, various forms of examinations or treatments are performed using catheters. A catheter can be percutaneously inserted into a blood vessel from a puncture site formed at a wrist, an inguinal region, and the like, and is carried through the blood vessel to a site to be examined or treated. After an examination or treatment by a healthcare worker is completed, an elongated insertion member such as a puncture needle, a catheter, and a sheath used to introduce the catheter into a living body is removed from the puncture site, and the puncture site is stopped from bleeding.

Japanese Patent Application Publication No. 2005-521464A discloses a dressing as a compression device that compresses a wound in a patient after a sheath is removed. The dressing disclosed in Japanese Patent Application Publication No. 2005-521464A includes an inflatable bladder having a deflated form in which a membrane is adjacent to an end wall and an inflated form in which the membrane is spaced apart from the end wall. In addition, the dressing disclosed in Japanese Patent Application Publication No. 2005-521464A includes a holding portion that holds the bladder against a skin of the patient at a position substantially covering the wound. Japanese Patent Application Publication No. 2005-521464A discloses that the holding portion includes a flexible web that is interlocked with the end wall of the bladder and protrudes outward from the end wall of the bladder, and an adhesive layer for adhering the flexible web to the skin of the patient is provided on a surface of the flexible web.

In the dressing as the compression device described in Japanese Patent Application Publication No. 2005-521464A, the adhesive layer as an adhesion surface provided on the surface of the flexible web is adhered to the skin as a biological surface of the patient, and the bladder constituting a pressing portion is brought into the inflated form, so that the wound of the patient can be compressed by the bladder.

The bladder in the inflated form of the dressing described in Japanese Patent Application Publication No. 2005-521464A has a configuration in which a central portion largely protrudes. Therefore, a compression force exerted by the central portion of the bladder tends to be larger than a compression force exerted by a peripheral portion of the bladder. Accordingly, it is difficult to uniformly compress, within a compression region, the biological surface that comes into contact with the bladder and is compressed by the bladder. When only the central portion of the bladder compresses the biological surface, the compression region is relatively small, and it may be difficult to compress a desired position on the biological surface.

SUMMARY

A compression device is disclosed that includes an inflatable portion capable of realizing a compression region with a relatively small difference in compression force over a relatively wide range.

According to a first aspect of this disclosure, a compression device includes: an adhesion surface configured to be adhered to a biological surface; and an inflatable portion configured to compress the biological surface. The inflatable portion defines an accommodation space capable of accommodating a fluid, and is capable of being inflated in a thickness direction from a flat deflated form and being changed to an inflated form by supplying the fluid to the accommodation space, and the inflatable portion is provided with an inflation restricting portion that is provided at a position sandwiched or surrounded by inflation regions inflatable in the thickness direction in a plan view viewed along the thickness direction, and in which inflation in the thickness direction is restricted by the inflation regions.

According to one embodiment of this disclosure, the inflation restricting portion is provided at a position including a center position of the accommodation space in the plan view viewed along the thickness direction.

According to one embodiment of this disclosure, a plurality of the inflation restricting portions are provided at positions separated from each other in the plan view viewed along the thickness direction.

According to one embodiment of this disclosure, the inflation restricting portion includes a straight line portion extending in a straight line shape in the plan view viewed along the thickness direction.

According to one embodiment of this disclosure, the inflatable portion defines the accommodation space between two members facing each other in the thickness direction, and the inflation restricting portion is formed by joining the two members in the thickness direction.

According to one embodiment of this disclosure, the two members are two sheet-shaped members that are stacked, and the accommodation space is defined by a central portion where the two sheet-shaped members are not joined to each other and that is surrounded by peripheral portions of the two sheet-shaped members that are joined to each other.

According to one embodiment of this disclosure, the compression device further includes: an adhesion body having the adhesion surface; and a compression member attached to the adhesion body and including the inflatable portion. The compression member includes an inflatable body including the inflatable portion, and a support body fixed to the adhesion body and configured to support the inflatable body. When the inflatable portion is a first inflatable portion, the inflatable body includes the first inflatable portion, and a second inflatable portion configured to press the first inflatable portion toward a biological surface by being inflated in a thickness direction from a flat deflated form and being changed to an inflated form in a state of being sandwiched between the support body and the first inflatable portion, and the second inflatable portion is not provided with the inflation restricting portion.

According to one embodiment of this disclosure, the inflatable body includes an extending portion extending from the first inflatable portion and the second inflatable portion, the support body defines a through-hole penetrating from one side to the other side in a direction orthogonal to the adhesion surface, the inflatable body is attached to the support body in a state in which the extending portion extends through the through-hole of the support body from the one side where the first inflatable portion and the second inflatable portion are located with the support body interposed between the first inflatable portion and the second inflatable portion to the other side and is wound around the support body.

According to second aspect of this disclosure, a compression device is disclosed that includes: an adhesion surface configured to be adhered to a biological surface; an inflatable portion configured to compress the biological surface; the inflatable portion defining an accommodation space configured to accommodate a fluid, the inflatable portion being configured to be inflated from a flat deflated form and to be changed to an inflated form by supplying the fluid to the accommodation space; and wherein the inflatable portion is provided with an inflation restricting portion, the inflation restricting portion configured to restrict inflation of the inflatable portion.

According to a third aspect of this disclosure, a method for compressing a biological surface is disclosed, which includes: adhering an adhesion surface to a biological surface; compressing the biological surface with an inflatable portion, the inflatable portion defining an accommodation space configured to accommodate a fluid, the inflatable portion being configured to be inflated in a thickness direction from a flat deflated form and to be changed to an inflated form by supplying the fluid to the accommodation space; and restricting the thickness direction of inflation regions of the inflatable portion by providing an inflation restricting portion, the inflation restricting portion being provided at a position sandwiched or surrounded by the inflation regions that are inflatable in the thickness direction.

According to this disclosure, a compression device is provided that includes an inflatable portion capable of realizing a compression region with a small difference in compression force over a relatively wide range.

BRIEF DESCRIPTION OF THE DRAWINGS

FIGS. 3A and 3B are side views of the compression device shown in FIG. 1, in which FIG. 3A shows a case where inflatable portions are in a deflated form, and FIG. 3B shows a case where the inflatable portions are in an inflated form.

DETAILED DESCRIPTION

Figure 1:
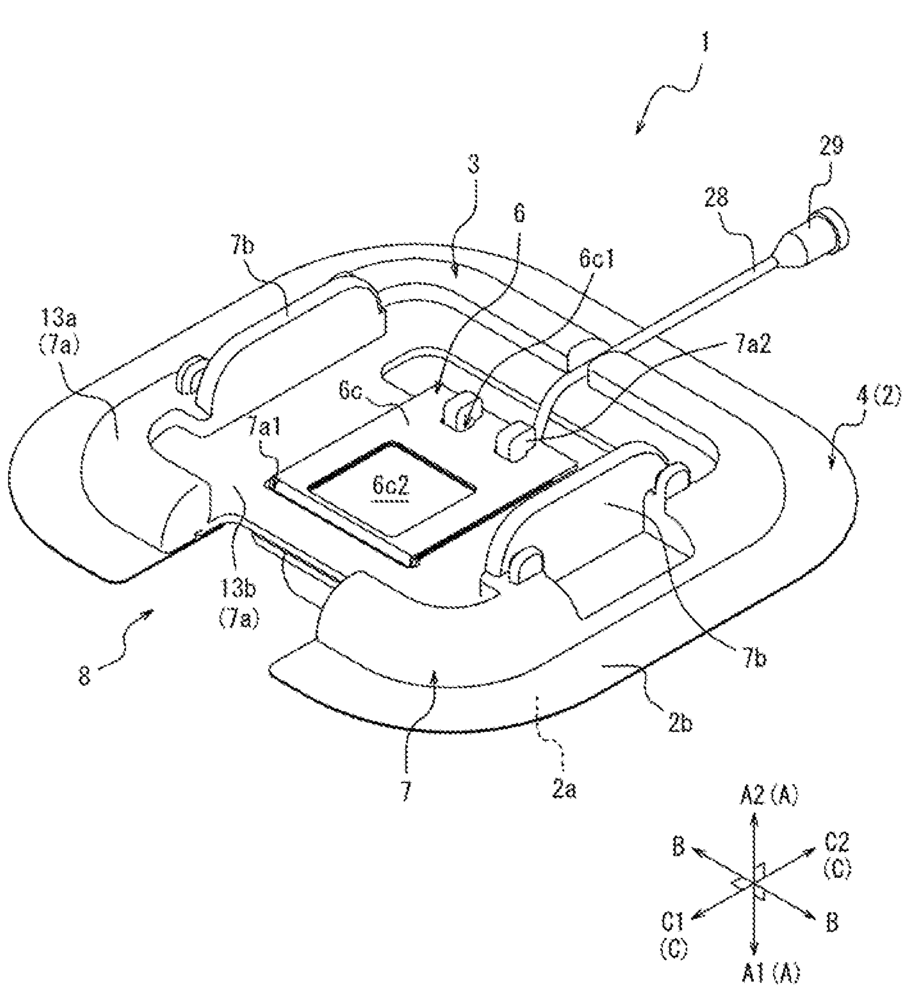
FIG. 1 is a perspective view of a compression device according to a first embodiment of this disclosure as viewed from an upper surface side.

Hereinafter, embodiments of a compression device according to this disclosure will be exemplified with reference to the drawings. In the drawings, common components are denoted by the same reference numerals.

First Embodiment

FIGS. 1 to 6 are views showing a compression device 1 according to an embodiment of this disclosure. Specifically, FIG. 1 is a perspective view of the compression device 1 as viewed from an upper surface side. FIGS. 2A and 2B are plan views of the compression device 1. Specifically, FIG. 2A is a top view of the compression device 1. FIG. 2B is a bottom view of the compression device 1. FIGS. 3A and 3B are side views of the compression device 1. FIG. 3A shows a case where inflatable portions 6*a* and 6*b* are in a deflated form. FIG. 3B shows a case where the inflatable portions 6*a* and 6*b* are in an inflated form. FIGS. 4A and 4B are cross-sectional views of the compression device 1 taken along a line I-I of FIGS. 2A and 2B. FIG. 4A is a cross-sectional view when the inflatable portions 6*a* and 6*b* are in the deflated form. FIG. 4B is a cross-sectional view when the inflatable portions 6*a* and 6*b* are in the inflated form. FIG.

Figures 3A, 3B:
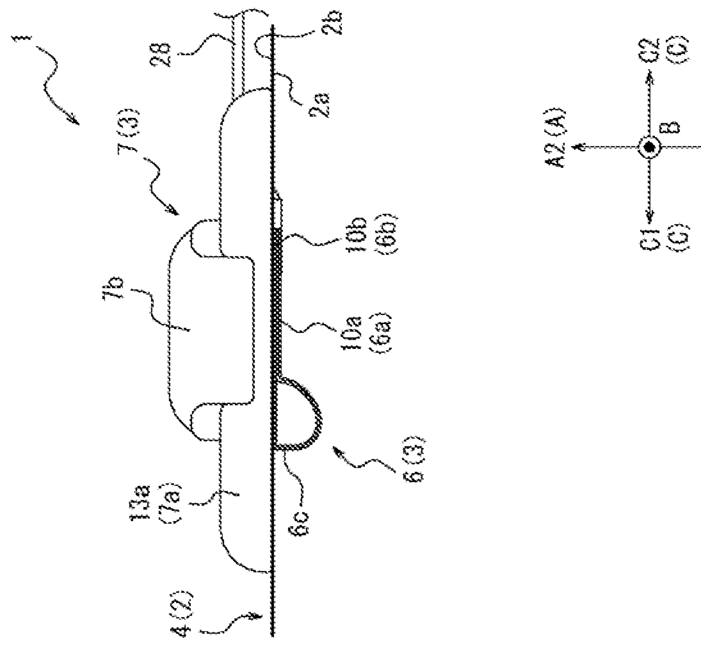
Figure 4A:
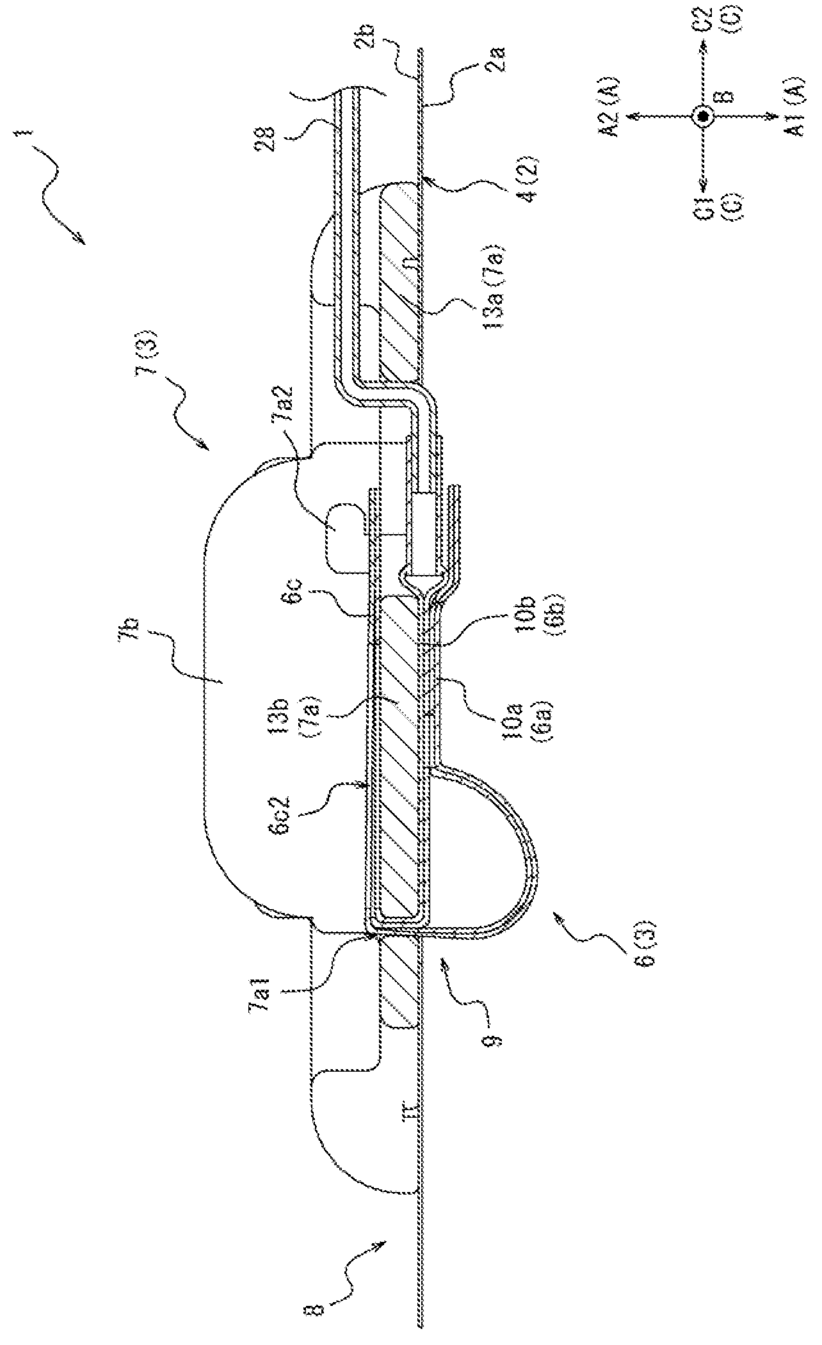
FIG. 4A is a cross-sectional view taken along a line I-I in FIGS. 2A and 2B, and is the cross-sectional view when the inflatable portions are in the deflated form.
Figure 4B:
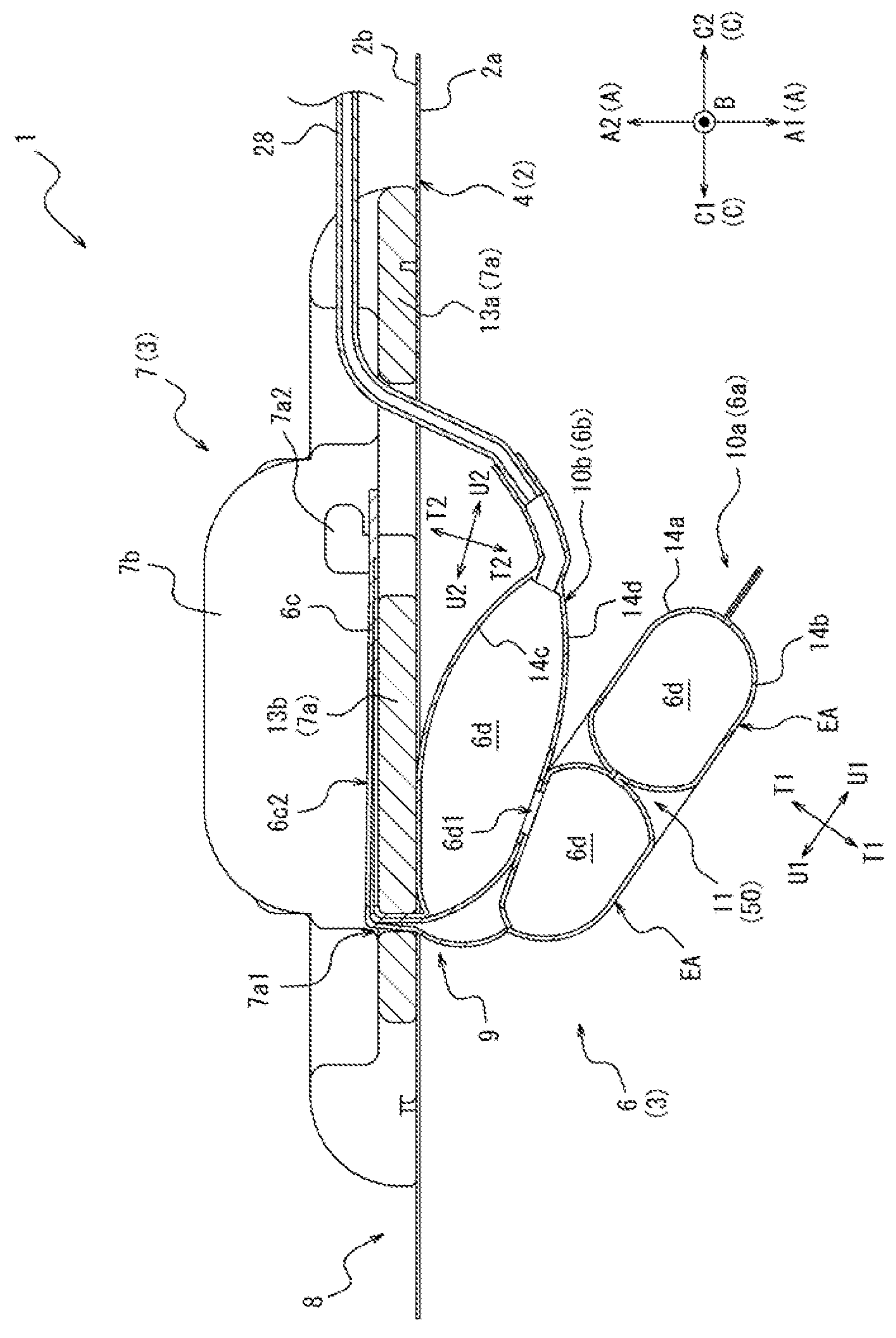
FIG. 4B is a cross-sectional view taken along the line I-I in FIGS. 2A and 2B, and is the cross-sectional view when the inflatable portions are in the inflated form.
Figure 6:
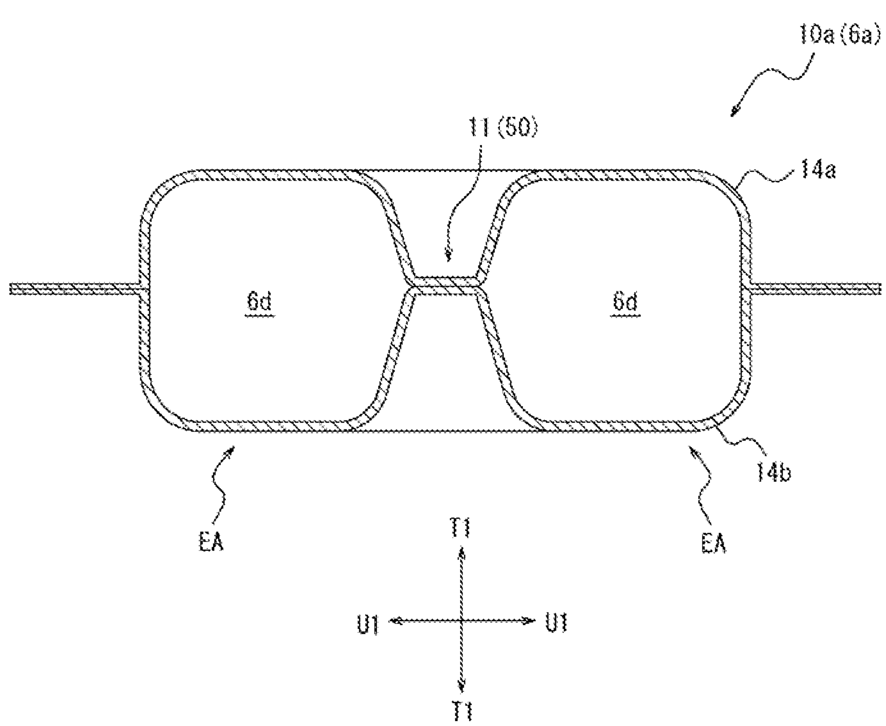
FIG. 6 is a cross-sectional view of the inflatable portions taken along a line II-II in FIG. 3B.

5 is a partially enlarged view of the inflatable portions 6*a* and 6*b* shown in FIG. 4B. FIG. 6 is a cross-sectional view of the inflatable portion 6*a* taken along a line II-II in FIG. 3B.

As shown in FIGS. 2A to 6, the compression device 1 includes an adhesion surface 2*a* that can be adhered to a biological surface and the inflatable portion 6*a* that can compress the biological surface. The compression device 1 is attached to the biological surface by adhering the adhesion surface 2*a* to the biological surface. The inflatable portion 6*a* can compress the biological surface in a state in which the adhesion surface 2*a* is adhered to the biological surface.

Figure 5:
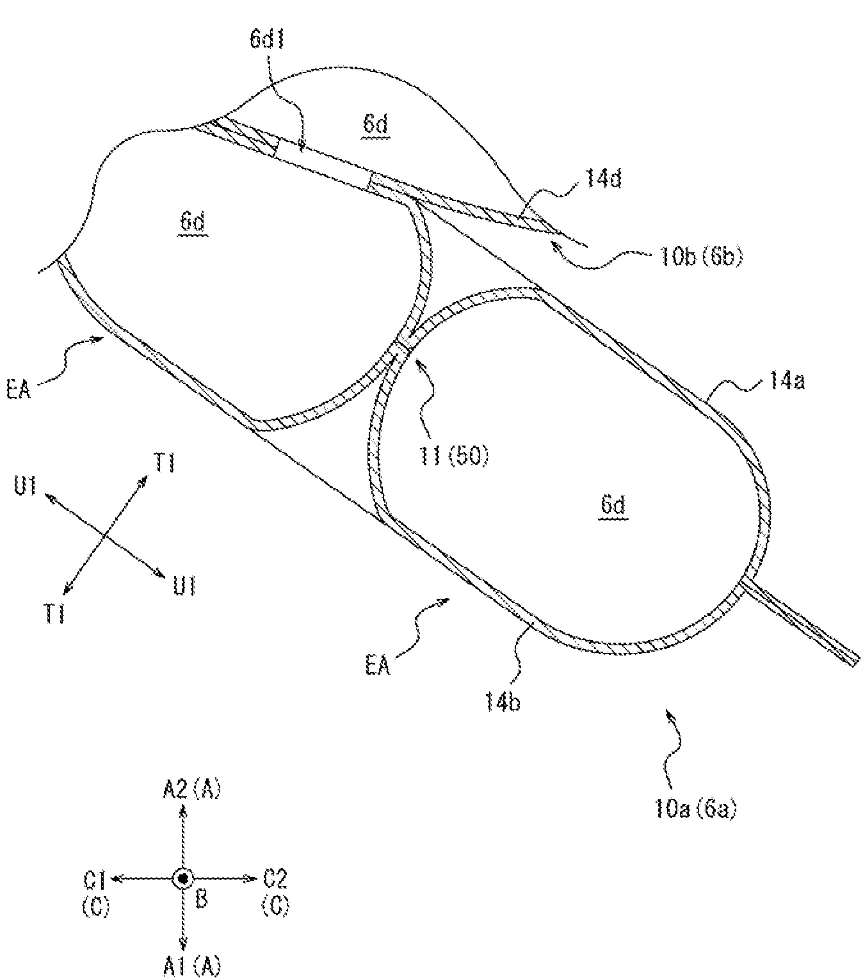
FIG. 5 is a partially enlarged view of the inflatable portions shown in FIG. 4B.

As shown in FIGS. 4B, 5, and 6, the inflatable portion 6*a* defines accommodation spaces 6*d* in which a fluid can be accommodated. As shown in FIGS. 3A, 3B, 4A, and 4B, the inflatable portion 6*a* can be inflated in a thickness direction T1 from a flat deflated form (see FIGS. 3A and 4A) and changed to an inflated form (see FIGS. 3B and 4B) by supplying the fluid to the accommodation spaces 6*d*. Hereinafter, for convenience of description, the thickness direction T1 of the inflatable portion 6*a* is referred to as the "thickness direction T1". An in-plane direction U1 of the inflatable portion 6*a* that is orthogonal to the thickness direction T1 is referred to as the "in-plane direction U1".

As shown in FIGS. 4B, 5, and 6, the inflatable portion 6*a* is provided with an inflation restricting portion 50. The inflation restricting portion 50 is provided at a position surrounded by inflation regions EA that can be inflated in the thickness direction T1 in a plan view (see FIG. 2B) viewed along the thickness direction T1. The inflation restricting portion 50 may be provided at a position sandwiched by (i.e., between) the inflation regions EA that can be inflated in the thickness direction T1 in the plan view (see FIG. 2B) viewed along the thickness direction T1. Inflation of the inflation restricting portion 50 in the thickness direction T1 is restricted by the inflation regions EA.

Although details will be described later, the inflatable portion 6*a* according to the present embodiment can be implemented by a first balloon portion 10*a* (see FIGS. 3A to 6). The compression device 1 according to the present embodiment further includes another inflatable portion 6*b* implemented by a second balloon portion 10*b* (see FIGS. 3A to 6). Hereinafter, for convenience of description, the inflatable portion 6*a* implemented by the first balloon portion 10*a* will be referred to as a "first inflatable portion 6*a*". The inflatable portion 6*b* implemented by the second balloon portion 10*b* will be referred to as a "second inflatable portion 6*b*". A thickness direction T2 of the second inflatable portion 6*b* is referred to as the "thickness direction T2". Further, an in-plane direction U2 of the second inflatable portion 6*b* that is orthogonal to the thickness direction T2 is referred to as the "in-plane direction U2".

Figures 2A, 2B:
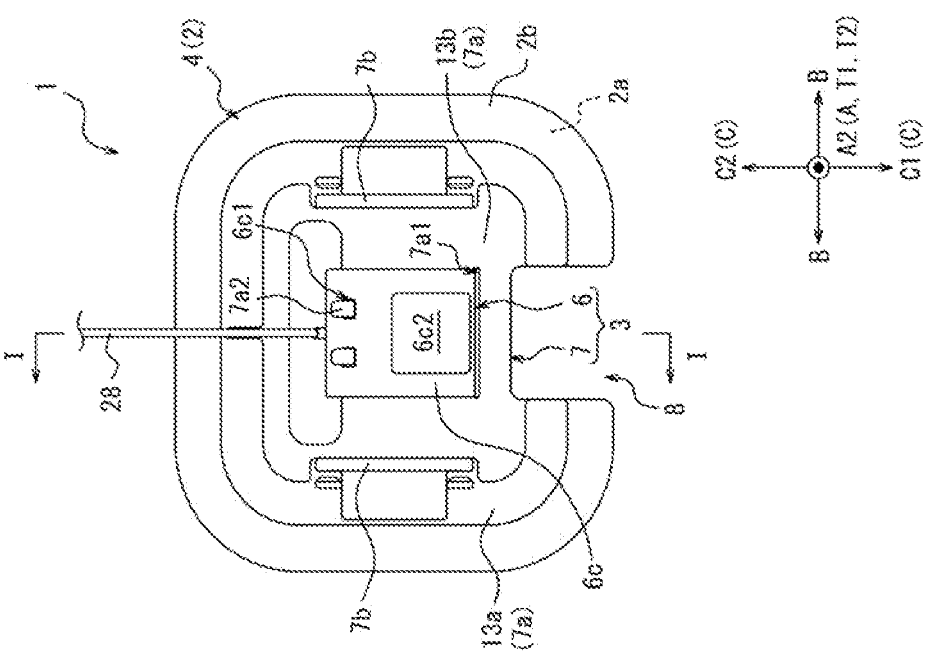
FIG. 2A is a top view of the compression device shown in FIG. 1.
FIG. 2B is a bottom view of the compression device shown in FIG. 1.

As shown in FIGS. 4B, 5, and 6, the first inflatable portion 6*a* implemented by the first balloon portion 10*a* includes a portion that is inflated in the thickness direction T1, and a portion that is provided at a position sandwiched by the inflatable portion in the in-plane direction U1 and is not inflated in the thickness direction T1. This non-inflatable portion can be, for example, a sheet joint portion 11 formed by welding, by heat sealing or the like, two sheet-shaped members 14*a* and 14*b* constituting the first balloon portion 10*a*. That is, at the sheet joint portion 11, the sheet-shaped members 14*a* and 14*b* are not separated from each other in the thickness direction T1 by being joined to each other. The inflation region EA according to the present embodiment is formed by a portion that is adjacent to the sheet joint portion 11 in the in-plane direction U1 and that is inflated in the thickness direction T1. As shown in FIG. 2B, this portion annularly surrounds the sheet joint portion 11 in the plan view. The inflation restricting portion 50 according to the present embodiment is implemented by the sheet joint portion 11.

By providing the inflation restricting portion 50 in the first inflatable portion 6*a*, it is possible to help prevent the formation of a portion where a protruding amount in the thickness direction T1 is locally increased in the inflated form in the in-plane direction U1, as compared with a configuration in which the inflation restricting portion 50 is not provided. Therefore, by using the first inflatable portion 6*a* provided with the inflation restricting portion 50, a compression region with a relatively small difference in compression force can be realized over a wide range.

In the present embodiment, although the inflation restricting portion 50 is implemented by the sheet joint portion 11, a specific configuration of the inflation restricting portion 50 is not particularly limited as long as inflation in the thickness direction T1 is restricted by a portion of the surrounding inflation region EA. Alternatively, as in the sheet joint portion 11 according to the present embodiment, it is preferable that a portion that is not inflated in the thickness direction T1 is formed by joining inner surfaces defining the accommodation space 6*d* by adhesion, welding, or the like. With such a configuration, the inflation restricting portion 50 can be rather easily realized, and a configuration of the first inflatable portion 6*a* is unlikely to be complicated.

The compression device 1 according to the present embodiment can include two inflatable portions (the first inflatable portion 6*a* and the second inflatable portion 6*b* in the present embodiment), but may include only one inflatable portion, or may include three or more inflatable portions. At least one inflatable portion may be provided with the above-described inflation restricting portion 50. The details will be described later, and when the compression device 1 includes a plurality of inflatable portions (the first inflatable portion 6*a* and the second inflatable portion 6*b* in the present embodiment) as in the present embodiment, it is preferable that the inflation restricting portion 50 is provided in at least one inflatable portion (the first inflatable portion 6*a* in the present embodiment) that comes into contact with the biological surface. Details of the inflation restricting portion 50 will be described later.

Hereinafter, further details of the compression device 1 according to the present embodiment will be described with reference to FIGS. 1 to 6.

The compression device 1 can include an adhesion body 2 and a compression member 3. The adhesion body 2 can include the adhesion surface 2*a* that can be adhered to the biological surface. The compression member 3 is fixed to the adhesion body 2. The compression member 3 can include the first inflatable portion 6*a* that can compress the biological surface in a state in which the adhesion surface 2*a* of the adhesion body 2 is adhered to the biological surface.

In a direction orthogonal to the adhesion surface 2*a*, a direction from a surface of the adhesion body 2 opposite to the surface on which the adhesion surface 2*a* is provided to the surface on which the adhesion surface 2*a* is provided is an adhesion direction in which the compression device 1 is adhered to the biological surface. Hereinafter, this direction is referred to as a "downward direction A1" or a "lower side" for convenience of description. In the direction orthogonal to the adhesion surface 2*a*, a direction opposite to the downward direction A1 is a separation direction in which the compression device 1 is separated from the biological surface. Hereinafter, for convenience of description, the direction that is orthogonal to the adhesion surface 2*a* and the direction opposite to the downward direction A1 is referred to as an "upward direction A2" or an "upper side".

Further, in plan views (see FIGS. 2A and 2B) of the compression device 1 viewed along the direction orthogonal to the adhesion surface 2*a*, the plan view (see FIG. 2A) viewed in the downward direction A1 from the upper side is referred to as a "top view" for convenience of description. In the plan views (see FIGS. 2A and 2B) of the compression device 1 viewed along the direction orthogonal to the adhesion surface 2*a*, the plan view (see FIG. 2B) viewed in the upward direction A2 from the lower side is referred to as a "bottom view" for convenience of description. In addition, when the top view and the bottom view are not distinguished from each other, each of the top view and the bottom view is referred to as the "plan view". In addition, unless otherwise specified, the descriptions of the "plan view", the "top view", and the "bottom view" mean a plan view, a top view, and a bottom view when the first inflatable portion 6*a* and the second inflatable portion 6*b* of the compression member 3 to be described later is in a deflated form.

As shown in FIGS. 1 to 4B, the adhesion body 2 according to the present embodiment is an adhesive sheet 4 including the adhesion surface 2*a* that can be adhered to the biological surface on a lower surface on one side in a thickness direction A. In the present embodiment, the above "direction orthogonal to the adhesion surface 2*a*" is a direction same as the thickness direction A of the adhesive sheet 4. The adhesion surface 2*a* is covered with a liner such as a release sheet in a state before use before being adhered to the biological surface. The liner can be peeled and removed immediately before the adhesion surface 2*a* is adhered to the biological surface. The adhesive sheet 4 as the adhesion body 2 shown in FIGS. 1 to 4B shows a use state in which the liner is removed and the adhesion surface 2*a* is exposed.

As shown in FIGS. 1 to 4B, the compression member 3 according to the present embodiment is fixed to the adhesive sheet 4. Specifically, the compression member 3 according to the present embodiment is fixed to a fixing surface 2*b* which is an upper surface of the adhesive sheet 4 on a side opposite to the adhesion surface 2*a*. The compression member 3 includes the first inflatable portion 6*a* and the second inflatable portion 6*b* that can compress, in a state in which the adhesion surface 2*a* is adhered to the biological surface, the biological surface at a position different from a position where the adhesion surface 2*a* is adhered.

Accordingly, the compression device 1 is fixed to a position on the biological surface by adhering the adhesion surface 2*a* on the biological surface. According to the compression device 1, a predetermined site on the biological surface can be compressed by the first inflatable portion 6*a* and the second inflatable portion 6*b* in a state in which the adhesion surface 2*a* is adhered to the biological surface. The predetermined site on the biological surface can include, for example, a wound on the biological surface or a vicinity of the wound formed by inserting a medical insertion member such as a puncture needle, a catheter, and a sheath into a blood vessel of a living body. After the medical insertion member is removed from the living body, the wound on the biological surface or the vicinity of the wound is compressed by the first inflatable portion 6*a* and the second inflatable portion 6*b*, so that a subcutaneous blood vessel or a perforation extending from the blood vessel to the biological surface can be pressed from the biological surface. By performing compression by the first inflatable portion 6*a* and the second inflatable portion 6*b* for a predetermined period, bleeding can be stopped. As described above, the compression device 1 according to the present embodiment can include the first inflatable portion 6*a* and the second inflatable portion 6*b*, but may not include the second inflatable portion 6*b*.

Adhesion Body 2

As described above, the adhesion body 2 according to the present embodiment is the adhesive sheet 4. The adhesive sheet 4 has flexibility. Therefore, the adhesive sheet 4 can be deformed according to a shape of the biological surface. In addition, the adhesion surface 2*a* rather easily follows deformation of the biological surface. As a result, it is possible to help prevent the compression device 1 from being unintentionally released from the biological surface.

The adhesion surface 2*a* of the adhesive sheet 4 according to the present embodiment is formed by the entire lower surface of the adhesive sheet 4. The adhesion surface 2*a* of the adhesive sheet 4 may be provided only in a partial region of the lower surface of the adhesive sheet 4.

The adhesive sheet 4 can include a plurality of layers including, for example, a base material layer and an adhesive layer.

The base material layer can be formed of, for example, a thin resin sheet. More specifically, the base material layer can be formed of, for example, a white spunlace nonwoven fabric (i.e., nonwoven fabric) of polyester fibers, and has a thickness in a range, for example, of 5 μm to 150 μm, and for example, 30 μm. However, a material of the base material layer is not limited to polyester, and an acrylic polymer, polyethylene, an ethylene-vinyl acetate copolymer, polyurethane, a polyamide derivative, and the like may be used.

The adhesive layer is formed of an adhesive such as a rubber-based adhesive, an acrylic-based adhesive, and a silicon-based adhesive. The adhesive layer can be stacked on the base material layer directly or indirectly with another layer interposed between the adhesive layer and the base material layer. The adhesion surface 2*a* of the adhesive sheet 4 according to the present embodiment is an adhesive layer.

The adhesive sheet 4 may further include another layer in addition to the base material layer and the adhesive layer. The adhesive sheet 4 may include, for example, a surface layer. The surface layer can be formed of, for example, a resin having a thickness of about 5 μm to 50 μm. More specifically, examples of a material of the surface layer include polyester, polyamide, polyamideimide, polyethylene, polypropylene, polycarbonate, polyurethane, polyvinyl chloride, and a fluororesin. The surface layer is stacked on the base material layer directly or indirectly with another layer interposed between the surface layer and the base material layer on a side opposite to the adhesive layer with the base material layer interposed between the surface layer and the adhesive layer. Therefore, the upper surface of the adhesive sheet 4 may be a surface layer.

More specifically, the adhesive sheet 4 may be formed of a nonwoven fabric tape having an adhesive agent as an adhesive on one surface of the nonwoven fabric tape. Further, the adhesive sheet 4 may be formed of a double-sided tape in which adhesive layers are provided on both sides of the base material layer. When the adhesive sheet 4 is formed of the double-sided tape, the compression member 3 can be fixed to the adhesive sheet 4 by adhering a support portion 7*a* of a support body 7 (to be described later) of the compression member 3 to one adhesive layer of the adhesive sheet 4.

The adhesive sheet 4 according to the present embodiment has a substantially C-shaped outer shape in the plan view (see FIGS. 2A and 2B). As shown in FIGS. 2A and 2B, the adhesive sheet 4 according to the present embodiment covers only a part of a lower surface side of the compression member 3. Specifically, the adhesive sheet 4 according to the present embodiment covers only an outer edge region of a lower surface of the compression member 3. The adhesive sheet 4 according to the present embodiment is fixed only to the outer edge region of the lower surface of the compression member 3. In other words, the adhesive sheet 4 according to the present embodiment does not cover a central region of the lower surface of the compression member 3 in which the first inflatable portion 6*a* of the compression member 3 is located. In addition, the adhesive sheet 4 according to the present embodiment does not cover the entire outer edge region of the lower surface of the compression member 3 and covers a part of the outer edge region. That is, the adhesive sheet 4 according to the present embodiment does not cover a part of the outer edge region of the lower surface of the compression member 3. According to the present embodiment, a portion of the outer edge region of the lower surface of the compression member 3 that is not covered with the adhesive sheet 4 is a portion adjacent to a receiving portion 8 in the compression member 3. The receiving portion 8 is a portion capable of receiving the medical insertion member (i.e., medical device) to be inserted or inserted into the blood vessel of the living body. The receiving portion 8 according to the present embodiment can be, for example, a gap defined by both ends of the adhesive sheet 4 having the substantially C-shape in the plan view.

Hereinafter, for convenience of description, in the plan views (see FIGS. 2A and 2B), a straight line direction connecting one end side where the receiving portion 8 is provided with the other end side opposite to the one end side may be referred to as a "front-rear direction C of the compression device 1" or as a "front-rear direction C". In the front-rear direction C, a direction from one end side where the receiving portion 8 is provided to the other end side may be referred to as a "rear direction C2", and an opposite direction of the rear direction C2, i.e., to one end side where the receiving portion 8 is provided to the other end side may be referred to as a "front direction C1". Further, in the plan views (see FIGS. 2A and 2B), a direction orthogonal to the front-rear direction C may be referred to as a "width direction B of the compression device 1" or as a "width direction B".

Compression Member 3

The compression member 3 according to the present embodiment includes an inflatable body 6 and the support body 7. Hereinafter, the inflatable body 6 and the support body 7 according to the present embodiment will be described.

The inflatable body 6 according to the present embodiment includes the first inflatable portion 6*a*, the second inflatable portion 6*b*, and an extending portion 6*c*.

The first inflatable portion 6*a* and the second inflatable portion 6*b* can press the biological surface in a state in which the adhesion surface 2*a* is adhered to the biological surface. Specifically, the first inflatable portion 6*a* and the second inflatable portion 6*b* according to the present embodiment can press the biological surface by extending in the thickness direction A orthogonal to the adhesion surface 2*a* in a state in which the adhesion surface 2*a* is adhered to the biological surface. The first inflatable portion 6*a* and the second inflatable portion 6*b* according to the present embodiment can press the biological surface at a position where the adhesive sheet 4 is not present in the plan view. That is, the first inflatable portion 6*a* and the second inflatable portion 6*b* according to the present embodiment can press the biological surface without the adhesive sheet 4 interposed between the inflatable portions 6*a*, 6*b* and the biological surface.

More specifically, as shown in FIGS. 3A and 4A, the first inflatable portion 6*a* and the second inflatable portion 6*b* according to the present embodiment are disposed to overlap each other in the thickness direction A. The first inflatable portion 6*a* is located on a lower side of the second inflatable portion 6*b*. When the first inflatable portion 6*a* and the second inflatable portion 6*b* are inflated in a state in which the adhesion surface 2*a* of the adhesion body 2 is adhered to the biological surface, the second inflatable portion 6*b* is inflated in the thickness direction A in a state of being sandwiched between the support body 7 to be described later and the first inflatable portion 6*a*. In other words, the second inflatable portion 6*b* presses the first inflatable portion 6*a* toward the biological surface by being inflated in the thickness direction T2 from a flat deflated form and being changed to an inflated form in the state of being sandwiched between the support body 7 and the first inflatable portion 6*a*. Therefore, the first inflatable portion 6*a* is pressed in the downward direction A1 by the support body 7 and the second inflatable portion 6*b*. That is, the first inflatable portion 6*a* is pressed toward the biological surface by the support body 7 and the second inflatable portion 6*b*.

The first inflatable portion 6*a* and the second inflatable portion 6*b* according to the present embodiment define the accommodation spaces 6*d* in which a fluid, for example, such as gas can be accommodated. More specifically, the first inflatable portion 6*a* and the second inflatable portion 6*b* according to the present embodiment are implemented by the first balloon portion 10*a* and the second balloon portion 10*b* which are interlocked with each other to allow internal communication. That is, the first inflatable portion 6*a* according to the present embodiment is implemented by the first balloon portion 10*a* located on the lower side. The second inflatable portion 6*b* according to the present embodiment is implemented by the second balloon portion 10*b* located on the upper side. The accommodation spaces 6*d* according to the present embodiment are implemented by internal spaces of the first balloon portion 10*a* and the second balloon portion 10*b* which communicate with each other through a communication hole 6*d*1.

The first inflatable portion 6*a* and the second inflatable portion 6*b* can be inflated toward the downward direction A1 in the thickness direction A by supplying the fluid to the accommodation spaces 6*d*. The first inflatable portion 6*a* and the second inflatable portion 6*b* according to the present embodiment are inflated toward the downward direction A1 by being changed from the deflated form (see FIGS. 3A and 4A) to the inflated form (see FIGS. 3B and 4B), and are in a posture (or shape) capable of compressing the biological surface. More specifically, when a fluid is supplied to the accommodation spaces 6*d*, the first inflatable portion 6*a* and the second inflatable portion 6*b* receive a reaction force from a lower surface of the support portion 7*a* of the support body 7 and are inflated toward the downward direction A1. The fluid supplied to the accommodation spaces 6*d* of the first inflatable portion 6*a* and the second inflatable portion 6*b* is not limited to gas, and may be, for example, a liquid.

As shown in FIGS. 3A and 4A, the first inflatable portion 6*a* and the second inflatable portion 6*b* in the deflated form are disposed along the lower surface of the support portion 7*a* of the support body 7 in a state in which the accommodation spaces 6*d* are deflated. The accommodation spaces 6*d* of the first inflatable portion 6*a* and the second inflatable portion 6*b* communicate with a tube 28 extending to an outside of the support body 7. A fluid, for example, such as air is supplied through the tube 28 to the accommodation spaces 6*d* of the first inflatable portion 6*a* and the second inflatable portion 6*b* from a fluid supply device connected to an inflation port as a connection portion 29 provided at an end portion of the tube 28. Accordingly, inflation states of the first inflatable portion 6*a* and the second inflatable portion 6*b* can be changed, and the first inflatable portion 6*a* and the second inflatable portion 6*b* can be changed from the deflated form (see FIGS. 3A and 4A) to the inflated form (see FIGS. 3B and 4B).

The first inflatable portion 6*a* and the second inflatable portion 6*b* according to the present embodiment are disposed between the biological surface and the lower surface of the support portion 7*a* in a state in which the adhesion surface 2*a* of the adhesive sheet 4 as the adhesion body 2 is adhered to the biological surface (hereinafter, may be referred to as an "adhering state of the compression device 1"). When the first inflatable portion 6*a* and the second inflatable portion 6*b* are inflated in the thickness direction A (inflated in the thickness directions T1 and T2, respectively, in the present embodiment) by the supply of the fluid in the adhering state of the compression device 1, the first inflatable portion 6*a* and the second inflatable portion 6*b* are sandwiched between the biological surface and the support portion 7*a* to press the biological surface. In other words, the first inflatable portion 6*a* and the second inflatable portion 6*b* in the deflated form in the present embodiment do not compress the biological surface in the adhering state of the compression device 1. Alternatively, the first inflatable portion 6*a* and the second inflatable portion 6*b* only need to be able to compress a predetermined site on the biological surface with a desired compression force by being changed from the deflated form to the inflated form in the adhering state of the compression device 1. That is, the first inflatable portion 6*a* and the second inflatable portion 6*b* in the deflated form may compress the biological surface in the adhering state of the compression device 1.

The extending portion 6*c* extends in a sheet shape from the first inflatable portion 6*a* and the second inflatable portion 6*b*. More specifically, the extending portion 6*c* includes two sheet portions extending from the first inflatable portion 6*a* and the second inflatable portion 6*b*, respectively, and a portion where the sheet portions are stacked and integrated. The extending portion 6*c* has flexibility. The extending portion 6*c* is wound around the support portion 7*a*. Accordingly, the extending portion 6*c* extends from the first inflatable portion 6*a* and the second inflatable portion 6*b* to an upper surface side of the support portion 7*a* on a side opposite to the first inflatable portion 6*a* and the second inflatable portion 6*b* with the support portion 7*a* interposed between the extending portion 6*c* and the inflatable portions 6*a*, 6*b* (i.e., the first inflatable portion 6*a* and the second inflatable portion 6*b*). The extending portion 6*c* is locked to the support portion 7*a* on the upper surface side of the support portion 7*a*.

Specifically, the support portion 7*a* according to the present embodiment defines a through-hole 7*a*1 penetrating from one side to the other side in the direction orthogonal to the adhesion surface 2*a*. That is, the through-hole 7*a*1 according to the present embodiment penetrates the support portion 7*a* of the support body 7 in the thickness direction A. The support portion 7*a* according to the present embodiment includes a locking protrusion 7*a*2 protruding in the upward direction A2. The extending portion 6*c* according to the present embodiment is wound around the support portion 7*a* through the through-hole 7*a*1. More specifically, the extending portion 6*c* according to the present embodiment extends through the through-hole 7*a*1 from the lower side at which the first inflatable portion 6*a* and the second inflatable portion 6*b* are located with the support portion 7*a* interposed between the extending portion 6*c* and the inflatable portions 6*a*, 6*b* (i.e., the first inflatable portion 6*a* and the second inflatable portion 6*b*) to the upper side opposite to the lower side. The extending portion 6*c* according to the present embodiment is wound around the support portion 7*a* along an inner surface of the support portion 7*a* that defines the through-hole 7*a*1 and an upper surface of the support portion 7*a*. A locking hole 6*c*1 into which the locking protrusion 7*a*2 is fitted is formed in the extending portion 6*c* on the upper surface side of the support portion 7*a*. By fitting the locking protrusion 7*a*2 into the locking hole 6*c*1, the extending portion 6*c* is positioned on the support portion 7*a*. The extending portion 6*c* is wound from a lower surface side to the upper surface side of the support portion 7*a* at a position on a receiving portion 8 side with respect to the first inflatable portion 6*a* and the second inflatable portion 6*b*. That is, the through-hole 7*a*1 according to the present embodiment is located on the receiving portion 8 side with respect to the first inflatable portion 6*a* and the second inflatable portion 6*b*. Therefore, in a cross-sectional view shown in FIG. 4A, the first inflatable portion 6*a*, the second inflatable portion 6*b*, and the extending portion 6*c* that constitute the inflatable body 6 according to the present embodiment are wound around the support portion 7*a*, so that a part of the first inflatable portion 6*a*, the second inflatable portion 6*b*, and the extending portion 6*c* protrude downward due to their stiffness, but the first inflatable portion 6*a*, the second inflatable portion 6*b*, and the extending portion 6*c* are curved in a substantially U shape as a whole. Accordingly, the first inflatable portion 6*a* and the second inflatable portion 6*b* can be inflated while pivoting about a hinge portion 9 (see FIGS. 4A and 4B), which is formed in a vicinity of a portion of the extending portion 6*c* wound around a lower edge portion of the through-hole 7*a*1.

The first inflatable portion 6*a* and the second inflatable portion 6*b* can be inflated not only toward the thickness direction A but also toward a direction inclined with respect to the thickness direction A by pivoting about the hinge portion 9 of the extending portion 6*c*. As described above, the inflatable body 6 according to the present embodiment is fixed to the support portion 7*a* in a state in which the extending portion 6*c* having the sheet shape is wound around the upper and lower surfaces of the support portion 7*a* through the through-hole 7*a*1 of the support portion 7*a* of the support body 7. Therefore, at the time of inflating, the first inflatable portion 6*a* and the second inflatable portion 6*b* are inflated while pivoting about, as a pivot center, the hinge portion 9 formed in the vicinity of the portion of the extending portion 6*c* wound around the lower edge portion of the through-hole 7*a*1.

More specifically, the first balloon portion 10*a* and the second balloon portion 10*b* that constitute the first inflatable portion 6*a* and the second inflatable portion 6*b* according to the present embodiment are disposed in a state of being overlapped with each other in the thickness direction A. One end of each of the first balloon portion 10*a* and the second balloon portion 10*b* is attached to the extending portion 6*c*. That is, one end side (a left side in FIGS. 3A, 3B, 4A, and 4B) of each of the first balloon portion 10*a* and the second balloon portion 10*b* is restrained by the extending portion 6*c*. Therefore, even when the first balloon portion 10*a* and the second balloon portion 10*b* are inflated, a distance between the first balloon portion 10*a* and the second balloon portion 10*b* in the thickness direction A is not increased on the one end side. On the other hand, the other end side (a right side in FIGS. 3A, 3B, 4A, and 4B) of each of the first balloon portion 10*a* and the second balloon portion 10*b* is not restrained at all. Therefore, when the first balloon portion 10*a* and the second balloon portion 10*b* are inflated, the distance between the first balloon portion 10*a* and the second balloon portion 10*b* in the thickness direction A is increased on the other end side. That is, in the first balloon portion 10*a* and the second balloon portion 10*b* that constitute the first inflatable portion 6*a* and the second inflatable portion 6*b* according to the present embodiment, with the one end side (the left side in FIGS. 3A, 3B, 4A, and 4B) attached to the extending portion 6*c* as a pivot center, the other end side (the right side in FIGS. 3A, 3B, 4A, and 4B) that is not attached to the extending portion 6*c* pivots about the pivot center. Accordingly, the first inflatable portion 6*a* and the second inflatable portion 6*b* according to the present embodiment are inflated toward the direction inclined with respect to the thickness direction A. However, a configuration for inflating the first inflatable portion 6*a* and the second inflatable portion 6*b* toward the direction inclined with respect to the thickness direction A is not limited to a configuration of the inflatable body 6 according to the present embodiment.

The first inflatable portion 6*a* is provided with the inflation restricting portion 50 as described above. Details of the inflation restricting portion 50 according to the present embodiment will be described later.

The inflatable body 6 according to the present embodiment can be formed of a member having transparency, and can be viewed in the direction orthogonal to the adhesion surface 2*a*. The same transparency applies to at least the support portion 7*a* of the support body 7 to be described later. Therefore, according to the compression device 1 in the present embodiment, a compression position on the biological surface can be visually recognized through the first inflatable portion 6*a*, the second inflatable portion 6*b*, and the extending portion 6*c* of the inflatable body 6, and the support portion 7*a* of the support body 7. Alternatively, as in the extending portion 6*c* according to the present embodiment, a visual recognition through-hole 6*c*2 may be provided to make it easier to visually recognize the compression position on the biological surface.

Constituent materials of the first inflatable portion 6*a*, the second inflatable portion 6*b*, and the extending portion 6*c* of the inflatable body 6 can include, for example, soft polyvinyl chloride, polyurethane, polyethylene, polypropylene, polyester, ethylene-vinyl acetate copolymer (EVA), silicone, or a material having flexibility obtained by mixing any of these materials.

As shown in FIGS. 4B, 5, and 6, the first inflatable portion 6*a* according to the present embodiment defines the accommodation spaces 6*d* between two members facing each other in the thickness direction T1. More specifically, the two members constituting the first inflatable portion 6*a* are two sheet-shaped members 14*a* and 14*b* that are stacked. That is, in the present embodiment, the two sheet-shaped members 14*a* and 14*b* are formed of the above-described resin material. The first inflatable portion 6*a* according to the present embodiment defines the accommodation spaces 6*d* in a central portion where the two sheet-shaped members 14*a* and 14*b* are not joined to each other and that is surrounded by peripheral portions of the two sheet-shaped members 14*a* and 14*b* that are joined to each other by heat sealing or the like. No folded portion is provided at the central portion of each of the two sheet-shaped members 14*a* and 14*b*. In other words, the first inflatable portion 6*a* according to the present embodiment is not configured to have a gore (i.e., side parts of a bag like object to sterically form the object). Alternatively, the first inflatable portion 6*a* may be configured to have a gore. The same configuration of not having a gore or having a gore applies to the second inflatable portion 6*b*. The second inflatable portion 6*b* according to the present embodiment is also implemented by two sheet-shaped members 14*c* and 14*d* formed of a resin material. The second inflatable portion 6*b* according to the present embodiment defines the accommodation spaces 6*d* in a central portion where the two sheet-shaped members 14*c* and 14*d* are not joined to each other and that is surrounded by peripheral portions of the two sheet-shaped members 14*c* and 14*d* that are joined to each other by heat sealing or the like.

The upper sheet-shaped member 14*a* constituting the first inflatable portion 6*a* is joined to the lower sheet-shaped member 14*d* constituting the second inflatable portion 6*b* on a front side in the front-rear direction C by heat sealing or the like. The communication hole 6*d*1 is formed in a joint portion between the upper sheet-shaped member 14*a* constituting the first inflatable portion 6*a* and the lower sheet-shaped member 14*d* constituting the second inflatable portion 6*b* to communicate with the accommodation spaces 6*d* defined by the first inflatable portion 6*a* and the second inflatable portion 6*b*.

As described above, the first inflatable portion 6*a* according to the present embodiment is implemented by the two sheet-shaped members 14*a* and 14*b*, but is not limited to this configuration. However, by constituting the first inflatable portion 6*a* by the two sheet-shaped members 14*a* and 14*b*, the simple first inflatable portion 6*a* can be easily realized. The constituting by the two sheet-shaped members 14*c* and 14*d* also applies to the second inflatable portion 6*b*.

In the first inflatable portion 6*a* according to the present embodiment, as described above, the peripheral portions of the two sheet-shaped members 14*a* and 14*b* are joined by heat sealing, but a joining method is not limited to heat sealing. The two sheet-shaped members 14*a* and 14*b* may be joined to each other by adhesion, welding other than heat sealing, or the like. However, the first inflatable portion 6*a* can be rather easily formed by forming the two sheet-shaped members 14*a* and 14*b* with the resin material and joining the two sheet-shaped members 14*a* and 14*b* by heat sealing. The forming the two sheet-shaped member 14*c* and 14*d* with a resin material and joining the two sheet-shaped members 14*c* and 14*d* by heat sealing also applies to the second inflatable portion 6*b*.

The support body 7 according to the present embodiment includes the support portion 7*a* and gripping portions 7*b*.

The support portion 7*a* extends from a position that overlaps with the adhesion surface 2*a* to a position that overlaps with the first inflatable portion 6*a* and the second inflatable portion 6*b* in the plan view. The support portion 7*a* is fixed to the adhesion body 2 by the fixing surface 2*b* which is a back side of the adhesion surface 2*a*. The support portion 7*a* supports the first inflatable portion 6*a* and the second inflatable portion 6*b*. According to the present embodiment, a portion of the support portion 7*a* that overlaps with the adhesion body 2 in the plan view is fixed to the fixing surface 2*b* of the adhesion body 2. In the present embodiment, a portion of the support portion 7*a* that does not overlap with the adhesion body 2 and overlaps with the first inflatable portion 6*a* and the second inflatable portion 6*b* in the plan view supports the first inflatable portion 6*a* and the second inflatable portion 6*b*.

More specifically, the support portion 7*a* according to the present embodiment includes an outer edge portion 13*a* fixed to the fixing surface 2*b* of the adhesive sheet 4 and extending in a substantially C-shape in the plan view, and a central portion 13*b* located inside the outer edge portion 13*a* in the plan view.

The outer edge portion 13*a* according to the present embodiment extends in the substantially C-shape such that a substantially entire region of outer edge portion 13*a* overlaps the adhesive sheet 4 in the plan view. The outer edge portion 13*a* according to the present embodiment is fixed to the fixing surface 2*b* which is the upper surface of the adhesive sheet 4. Both ends of the adhesive sheet 4 and the outer edge portion 13*a* that extend in the substantially C-shape in the plan view define a gap between both ends. The gap constitutes the receiving portion 8 of the compression device 1 capable of receiving the medical insertion member to be inserted or inserted into the blood vessel of the living body.

The receiving portion 8 according to the present embodiment is implemented by the gap between both of the ends of the adhesive sheet 4 and the outer edge portion 13*a*, and a configuration of the receiving portion 8 is not particularly limited. The receiving portion 8 may be implemented by a concave portion formed in an outer edge of the compression device 1 in the plan view.

The central portion 13*b* according to the present embodiment includes the portion of the support portion 7*a* that overlaps with the first inflatable portion 6*a* and the second inflatable portion 6*b* in the plan view and supports the first inflatable portion 6*a* and the second inflatable portion 6*b*. The above-described through-hole 7*a*1 is formed in the central portion 13*b*. The central portion 13*b* includes the above-described locking protrusion 7*a*2 that is fitted into the locking hole 6*c*1 of the extending portion 6*c* of the inflatable body 6. The first inflatable portion 6*a* and the second inflatable portion 6*b* of the inflatable body 6 described above are disposed on a lower surface side of the central portion 13*b*.

Accordingly, in the present embodiment, only a lower surface of the outer edge portion 13*a* of the support portion 7*a* is fixed to the fixing surface 2*b* of the adhesive sheet 4 having the substantially C-shape in the plan view. In other words, a lower surface of the central portion 13*b* of the support portion 7*a* is not covered with the adhesive sheet 4. Therefore, the lower surface of the central portion 13*b* of the support portion 7*a* is not fixed to the fixing surface 2*b* of the adhesive sheet 4.

The first inflatable portion 6*a* and the second inflatable portion 6*b* in the inflated form are sandwiched between the central portion 13*b* of the support portion 7*a* and the biological surface. Specifically, the central portion 13*b* of the support portion 7*a* according to the present embodiment includes a portion located above the first inflatable portion 6*a* and the second inflatable portion 6*b*. Therefore, when the first inflatable portion 6*a* and the second inflatable portion 6*b* are inflated in a state in which the adhesion surface 2*a* of the adhesion body 2 is adhered to the biological surface, the first inflatable portion 6*a* and the second inflatable portion 6*b* are sandwiched between the central portion 13*b* of the support portion 7*a* and the biological surface from above and below. Accordingly, the biological surface is compressed by the first inflatable portion 6*a* and the second inflatable portion 6*b*.

The support portion 7*a* according to the present embodiment is flat in the thickness direction A and has a substantially quadrangular outer shape in the plan view, and the shape of the support portion 7*a* is not particularly limited. In the support portion 7*a* according to the present embodiment, a maximum thickness in the thickness direction A is larger at the outer edge portion 13*a* than at the central portion 13*b*, but a thickness relation of the support portion 7*a* is not particularly limited.

The gripping portions 7*b* protrude in the upward direction A2 from the support portion 7*a*. Specifically, the gripping portions 7*b* according to the present embodiment protrude in the upward direction A2 from the outer edge portion 13*a* of the support portion 7*a*. The gripping portions 7*b* can be gripped by a healthcare worker. By providing the gripping portions 7*b*, the compression device 1 can be easily held. Therefore, it is possible to improve the operability of the healthcare worker.

More specifically, the support body 7 according to the present embodiment includes two gripping portions 7*b* disposed to face each other. The healthcare worker can rather easily hold the compression device 1 by holding the two gripping portions 7*b* disposed to face each other. The two gripping portions 7*b* according to the present embodiment include two grasping plate portions disposed to face each other in the width direction B.

Examples of a material of the support body 7 according to the present embodiment include a resin material. Examples of the resin material can include thermoplastic resins used in injection molding such as an ABS resin, an AS resin, polyethylene, polypropylene, polystyrene, polyvinyl chloride, a polyvinylidene chloride resin, polyphenylene oxide, thermoplastic polyurethane, polymethylene methacrylate, polyoxyethylene, a fluororesin, polycarbonate, polyamide, an acetal resin, an acrylic resin, and polyethylene terephthalate, and thermosetting resins such as a phenol resin, an epoxy resin, a silicone resin, and unsaturated polyester.

Inflation Restricting Portion 50 of First Inflatable Portion 6*a*

Next, details of the inflation restricting portion 50 provided in the first inflatable portion 6*a* according to the present embodiment will be described.

As described above, the inflation restricting portion 50 is provided at a position surrounded by the inflation regions EA that can be inflated in the thickness direction T1 in the plan view (see FIG. 2B) viewed along the thickness direction T1 of the first inflatable portion 6*a*. Specifically, the inflation restricting portion 50 according to the present embodiment is implemented by the sheet joint portion 11 in which the two sheet-shaped members 14*a* and 14*b* as two members are joined in the thickness direction T1. That is, the inflation restricting portion 50 according to the present embodiment is a portion that is not inflated in the thickness direction T1. By constituting the inflation restricting portion 50 by the sheet joint portion 11, the inflation restricting portion 50 can be rather easily formed.

In the present embodiment, the sheet joint portion 11 is formed by heat sealing the two sheet-shaped members 14*a* and 14*b*, but the configuration is not limited to heat sealing. The sheet joint portion 11 may be formed by joining the two sheet-shaped members 14*a* and 14*b* together by another joining method such as adhesion.

As shown in FIG. 2B, the inflation restricting portion 50 according to the present embodiment is provided at a position including a center position of the accommodation spaces 6*d* in the plan view viewed along the thickness direction T1 (the same direction as the thickness direction A in FIG. 2B). Specifically, the accommodation space 6*d* defined by the first inflatable portion 6*a* according to the present embodiment has a substantially rectangular outer edge in the plan view viewed along the thickness direction T1. The center position of the accommodation spaces 6*d* defined by the first inflatable portion 6*a* in the plan view viewed along the thickness direction T1 means a position of an intersection of two diagonal lines that are specified from the rectangular outer edge of the accommodation space 6*d*. That is, the sheet joint portion 11 as the inflation restricting portion 50 according to the present embodiment is provided at a position including the intersection of the two diagonal lines of the rectangular accommodation space 6*d* defined by the first inflatable portion 6*a* in the plan view viewed along the thickness direction T1.

As described above, by providing the inflation restricting portion 50 at the position including the center position of the accommodation spaces 6*d* defined by the first inflatable portion 6*a* in the plan view viewed along the thickness direction T1, it is possible to help prevent the protrusion of the center position that is most likely to protrude in the thickness direction T1. Therefore, a protruding amount in the thickness direction T1 can be relatively easily made uniform over a wide range in the in-plane direction U1. As a result, it is rather easy to realize the compression region with the small difference in the compression force over the wide range in the in-plane direction U1.

However, the inflation restricting portion 50 may not be provided at the above-described center position. The position of the inflation restricting portion 50 in the plan view viewed along the thickness direction T1 may be appropriately changed according to the shape of the biological surface to be compressed by the first inflatable portion 6*a*. Details of a configuration in which the inflation restricting portion 50 is not provided at the center position of the accommodation spaces 6*d* defined by the first inflatable portion 6*a* in the plan view viewed along the thickness direction T1 will be described later (see FIGS. 7 to 10B, 13, 14A, and 14B).

Further, in the compression device 1 according to the present embodiment, the first inflatable portion 6*a* is provided with the inflation restricting portion 50, and the second inflatable portion 6*b* is not provided with the inflation restricting portion 50. As described above, by providing the first inflatable portion 6*a* with the inflation restricting portion 50, it is possible to uniformly compress a wide range of the biological surface, as compared with the configuration in which the inflation restricting portion 50 is not provided. On the other hand, a maximum protruding amount of the first inflatable portion 6*a* in the thickness direction T1 is smaller than that in the configuration in which the inflation restricting portion 50 is not provided. Therefore, it may be difficult to apply a compression that requires a high compression force, such as a compression that deeply presses the biological surface, using only the first inflatable portion 6*a*. In the present embodiment, the first inflatable portion 6*a* provided with the inflation restricting portion 50 is pressed toward the biological surface by the second inflatable portion 6*b* not provided with the inflation restricting portion 50. Therefore, the first inflatable portion 6*a* can compress a wide range of the biological surface with a relatively uniform high compression force.

As described above, the inflatable body 6 according to the present embodiment is attached to the support body 7 in a state in which the extending portion 6*c* extends through the through-hole 7*a*1 of the support body 7 from one side (the lower side in the present embodiment) where the first inflatable portion 6*a* and the second inflatable portion 6*b* are located with the support body 7 interposed between the extending portion 6*c* and the inflatable body 6 (i.e., the first inflatable portion 6*a* and the second inflatable portion 6*b*) to the other side (the upper side in the present embodiment) and is wound around the support body 7 (refer to FIG. 4A and the like). Therefore, as described above, the first inflatable portion 6*a* according to the present embodiment is inflated to pivot about the hinge portion 9 (see FIGS. 4A and 4B). Since the first inflatable portion 6*a* according to the present embodiment is provided with the inflation restricting portion 50, even in a configuration in which the first inflatable portion 6*a* is inflated while pivoting as in the present embodiment, the first inflatable portion 6*a* can rather easily follow the biological surface and a uniform compression force can be obtained over a relatively wider range, as compared with the configuration in which the inflation restricting portion 50 is not provided.

Second Embodiment

Next, a compression device 101 according to a second embodiment of this disclosure will be described with reference to FIGS. 7, 8A, and 8B. The compression device 101 according to the second embodiment differs from the compression device 1 according to the first embodiment described above only in a configuration of a first inflatable portion 106*a*, and other configurations are the same. Therefore, only the configuration of the first inflatable portion 106*a* will be described here, and the description of the other configurations will be omitted.

Figure 7:
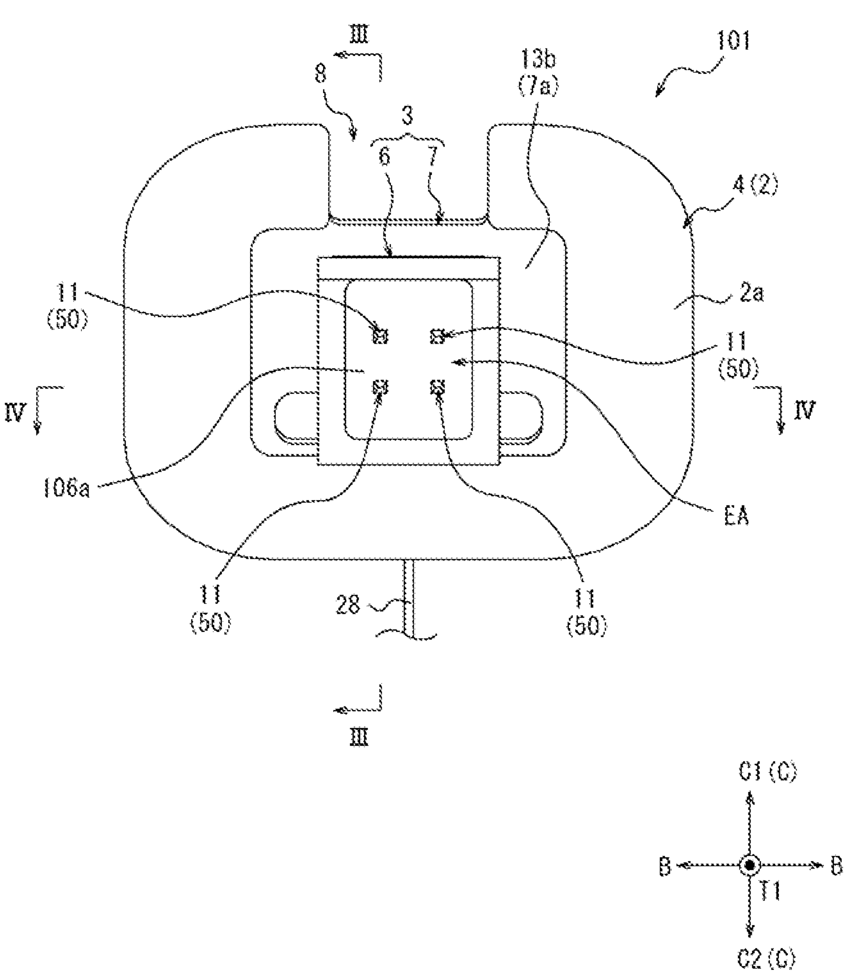
FIG. 7 is a plan view of a compression device according to a second embodiment of this disclosure viewed along a thickness direction of a first inflatable portion in an inflated form.

FIG. 7 is a diagram showing a case where the first inflatable portion 106*a* of the compression device 101 is in the inflated form. FIG. 7 is a plan view of the first inflatable portion 106*a* viewed along the thickness direction T1. FIG. 8A is a cross-sectional view of the first inflatable portion 106*a* taken along a line III-III in FIG. 7. FIG. 8B is a cross-sectional view of the first inflatable portion 106*a* taken along a line IV-IV in FIG. 7.

Figure 8A:
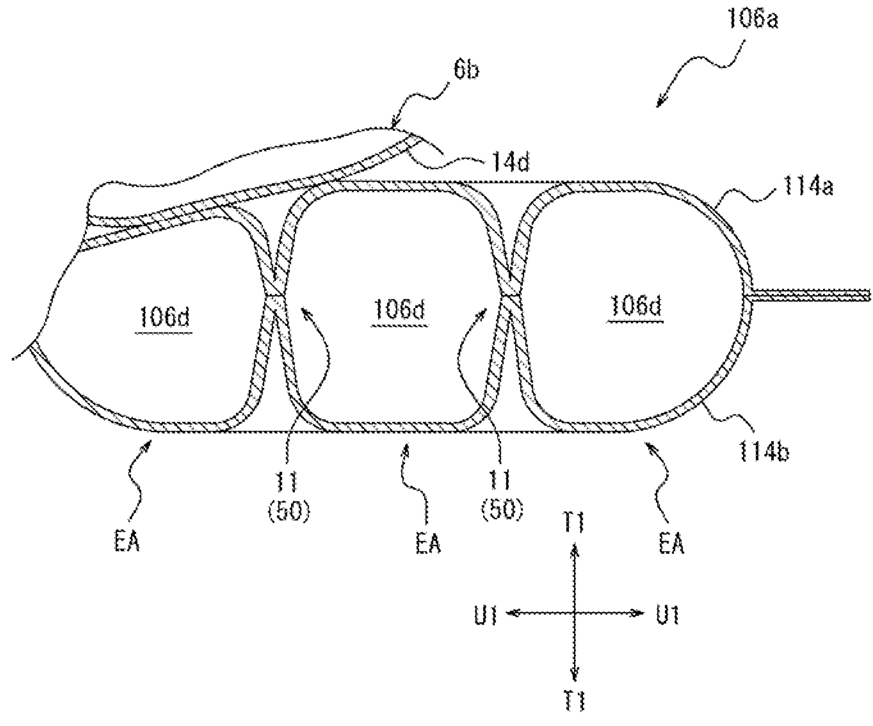
FIG. 8A is a cross-sectional view of the first inflatable portion taken along a line III-III in FIG. 7.
Figure 8B:
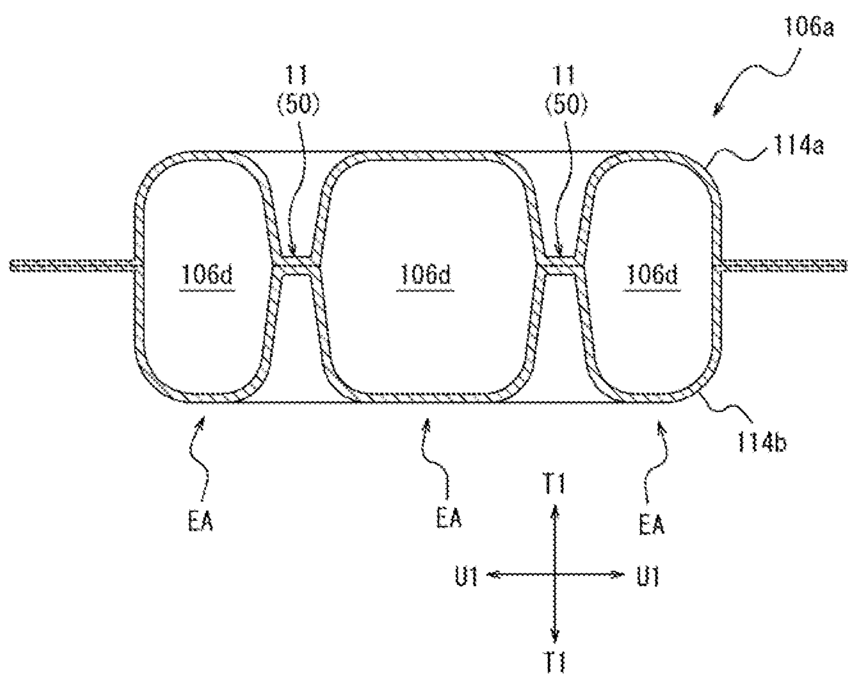
FIG. 8B is a cross-sectional view of the first inflatable portion taken along a line IV-IV in FIG. 7.

As shown in FIGS. 8A and 8B, the first inflatable portion 106*a* according to the present embodiment defines accommodation spaces 106*d* between two members facing each other in the thickness direction T1. More specifically, the two members constituting the first inflatable portion 106*a* are two sheet-shaped members 114*a* and 114*b* that are stacked. In the present embodiment, the two sheet-shaped members 114*a* and 114*b* are formed of the resin material. The first inflatable portion 106*a* according to the present embodiment defines the accommodation spaces 106*d* in a central portion where the two sheet-shaped members 114*a* and 114*b* are not joined to each other and are surrounded by peripheral portions of the two sheet-shaped members 114*a* and 114*b* that are joined to each other by heat sealing or the like. No folded portion is provided at the central portion of each of the two sheet-shaped members 114*a* and 114*b*. In other words, the first inflatable portion 106*a* according to the present embodiment is not configured to have a gore. Alternatively, the first inflatable portion 106*a* may be configured to have a gore.

The upper sheet-shaped member 114*a* constituting the first inflatable portion 106*a* is joined to the lower sheet-shaped member 14*d* constituting the second inflatable portion 6*b* on a front side in the front-rear direction C by heat sealing or the like. As in the first embodiment, the communication hole 6*d*1 (see FIG. 5 and the like) is formed in a joint portion between the upper sheet-shaped member 114*a* constituting the first inflatable portion 106*a* and the lower sheet-shaped member 14*d* constituting the second inflatable portion 6*b* to communicate with the accommodation spaces 106*d* defined by the first inflatable portion 106*a* and the second inflatable portion 6*b*.

As described above, the first inflatable portion 106*a* according to the present embodiment is implemented by the two sheet-shaped members 114*a* and 114*b*, but is not limited to this configuration. However, by constituting the first inflatable portion 106*a* by the two sheet-shaped members 114*a* and 114*b*, the first inflatable portion 106*a* can be rather easily realized.

In the first inflatable portion 106*a* according to the present embodiment, as described above, peripheral portions of the two sheet-shaped members 114*a* and 114*b* are joined by heat sealing, but the joining method is not limited to heat sealing. The two sheet-shaped members 114*a* and 114*b* may be joined to each other by adhesion, welding other than heat sealing, or the like. However, the first inflatable portion 106*a* can be rather easily formed by forming the two sheet-shaped members 114*a* and 114*b* with the resin material and joining the two sheet-shaped members 114*a* and 114*b* by heat sealing.

As shown in FIG. 7, the first inflatable portion 106*a* is provided with a plurality of inflation restricting portions 50 at positions separated from each other in the plan view viewed along the thickness direction T1. Specifically, the first inflatable portion 106*a* according to the present embodiment includes four inflation restricting portions 50. Thus, by providing the plurality of inflation restricting portions 50, the distribution of the compression force within the compression region is rather easily adjusted. The positions at which the inflation restricting portions 50 are provided may be appropriately determined according to the shape of the biological surface to be compressed by the first inflatable portion 106*a*. Alternatively, in order to make the distribution of the compression force uniform within the compression region, the plurality of inflation restricting portions 50 are preferably disposed in a distributed manner in the plan view viewed along the thickness direction T1. In the present embodiment, as an example, four inflation restricting portions 50 are disposed in a distributed manner. Specifically, the four inflation restricting portions 50 according to the present embodiment are provided at positions corresponding to four vertices of a square shape having a center position of the accommodation spaces 106*d* as an intersection of two diagonal lines in the plan view viewed along the thickness direction T1. In other words, in the plan view along the thickness direction T1, when a virtual straight line passing through any two inflation restricting portions 50 is defined, the four inflation restricting portions 50 according to the present embodiment include at least one (two in the present embodiment) inflation restricting portion 50 not located on this virtual straight line.

As in the first embodiment, each of the inflation restricting portions 50 is implemented by the sheet joint portion 11. Each of the inflation restricting portions 50 is not limited to the configuration of the sheet joint portion 11 formed by joining the sheet-shaped members 114*a* and 114*b* by heat sealing or the like, as long as the inflation in the thickness direction T1 is restricted as compared with the inflation region EA located around the inflation restricting portion 50 in the plan view viewed along the thickness direction T1. However, as described above, by constituting the inflation restricting portion 50 by the sheet joint portion 11, the inflation restricting portion 50 can be rather easily formed.

Third Embodiment

Next, a compression device 201 according to a third embodiment of this disclosure will be described with reference to FIGS. 9, 10A, and 10B. The compression device 201 according to the third embodiment differs from the compression device 1 according to the first embodiment described above only in a configuration of a first inflatable portion 206*a*, and the other configurations are the same. Therefore, only the configuration of the first inflatable portion 206*a* will be described here, and the description of the other configurations will be omitted.

Figure 9:
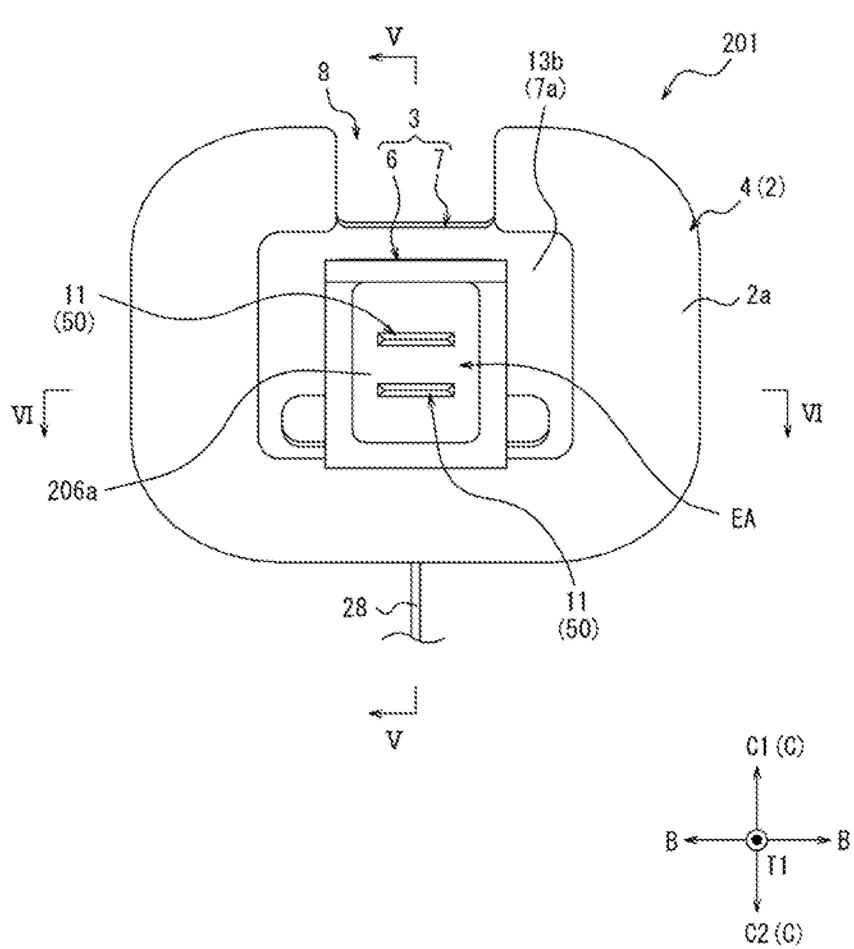
FIG. 9 is a plan view of a compression device according to a third embodiment of this disclosure viewed along a thickness direction of a first inflatable portion in an inflated form.

FIG. 9 is a diagram showing a case where the first inflatable portion 206*a* of the compression device 201 is in the inflated form. FIG. 9 is a plan view of the first inflatable portion 206*a* viewed along the thickness direction T1. FIG. 10A is a cross-sectional view of the first inflatable portion 206*a* taken along a line V-V in FIG. 9. FIG. 10B is a cross-sectional view of the first inflatable portion 206*a* taken along a line VI-VI in FIG. 9.

Figure 10A:
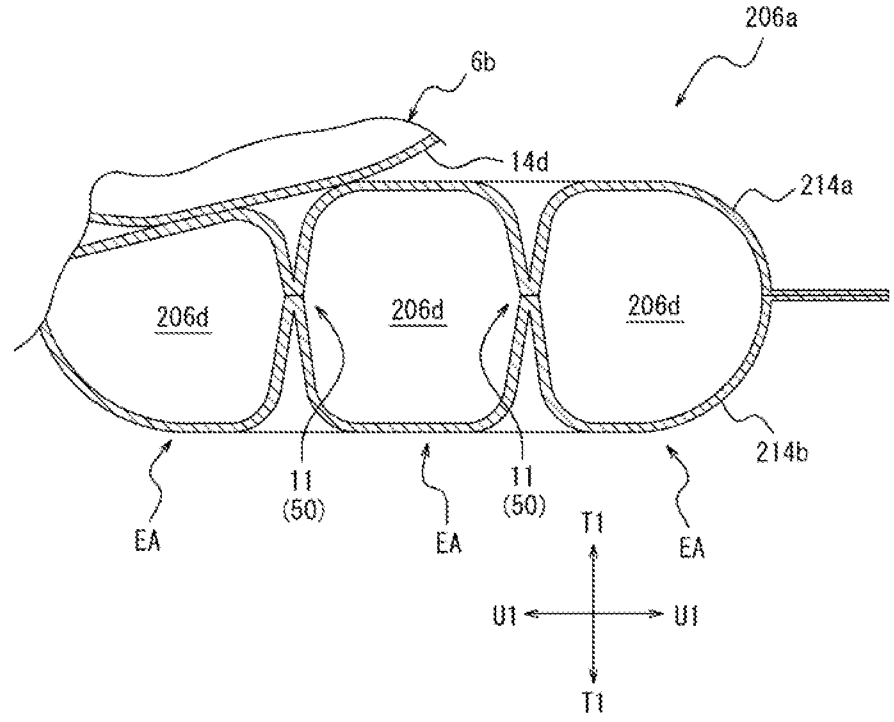
FIG. 10A is a cross-sectional view of the first inflatable portion taken along a line V-V in FIG. 9.
Figure 10B:
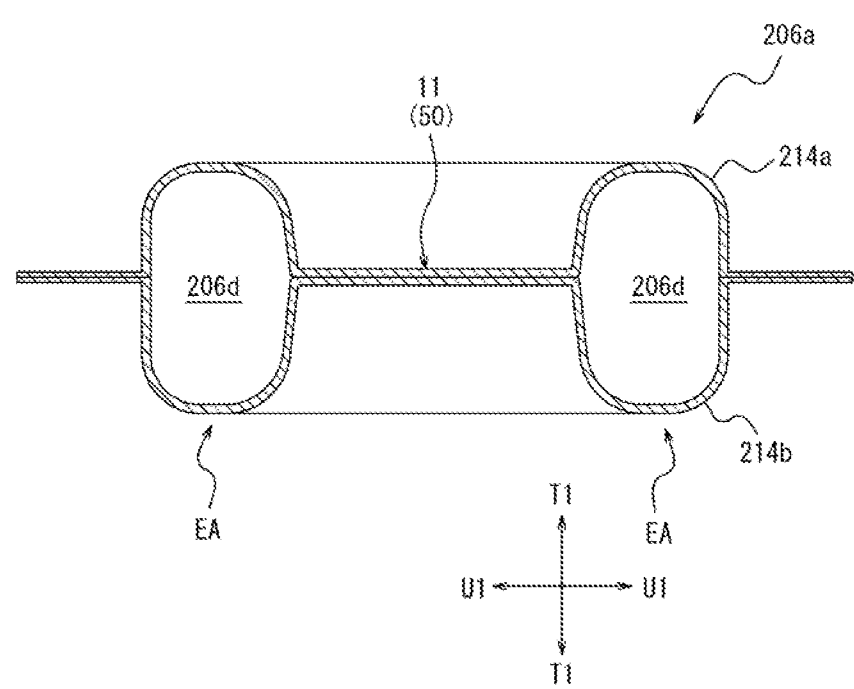
FIG. 10B is a cross-sectional view of the first inflatable portion taken along a line VI-VI in FIG. 9.

As shown in FIGS. 10A and 10B, the first inflatable portion 206*a* according to the present embodiment defines accommodation spaces 206*d* between two members facing each other in the thickness direction T1. More specifically, the two members constituting the first inflatable portion 206*a* are two sheet-shaped members 214*a* and 214*b* that are stacked. In the present embodiment, the two sheet-shaped members 214*a* and 214*b* are formed of the resin material. The first inflatable portion 206*a* according to the present embodiment defines the accommodation spaces 206*d* in a central portion where the two sheet-shaped members 214*a* and 214*b* are not joined to each other and that is surrounded by peripheral portions of the two sheet-shaped members 214*a* and 214*b* that are joined to each other by heat sealing or the like. No folded portion is provided at the central portion of each of the two sheet-shaped members 214*a* and 214*b*. In other words, the first inflatable portion 206*a* according to the present embodiment is not configured to have a gore. Alternatively, the first inflatable portion 206*a* may be configured to have a gore.

The upper sheet-shaped member 214*a* constituting the first inflatable portion 206*a* is joined to the lower sheet-shaped member 14*d* constituting the second inflatable portion 6*b* on a front side in the front-rear direction C by heat sealing or the like. As in the first embodiment, the communication hole 6*d*1 (see FIG. 5) is formed in a joint portion between the upper sheet-shaped member 214*a* constituting the first inflatable portion 206*a* and the lower sheet-shaped member 14*d* constituting the second inflatable portion 6*b* to communicate with the accommodation spaces 206*d* defined by the first inflatable portion 206*a* and the second inflatable portion 6*b*.

As described above, the first inflatable portion 206*a* according to the present embodiment is implemented by the two sheet-shaped members 214*a* and 214*b*, but is not limited to this configuration. However, by constituting the first inflatable portion 206*a* by the two sheet-shaped members 214*a* and 214*b*, the first inflatable portion 206*a* can be rather easily realized.

In the first inflatable portion 206*a* according to the present embodiment, as described above, peripheral portions of the two sheet-shaped members 214*a* and 214*b* are joined by heat sealing, but the joining method is not limited to heat sealing. The two sheet-shaped members 214*a* and 214*b* may be joined to each other by adhesion, welding other than heat sealing, or the like. However, the first inflatable portion 206*a* can be rather easily formed by forming the two sheet-shaped members 214*a* and 214*b* with the resin material and joining the two sheet-shaped members 214*a* and 214*b* by heat sealing.

As shown in FIG. 9, the first inflatable portion 206*a* is provided with the plurality of inflation restricting portions 50 at positions separated from each other in the plan view viewed along the thickness direction T1. Specifically, the first inflatable portion 206a according to the present embodiment includes two inflation restricting portions 50. Thus, by providing the plurality of inflation restricting portions 50, the distribution of the compression force within the compression region is rather easily adjusted. The positions at which the inflation restricting portions 50 are provided may be appropriately determined according to the shape of the biological surface to be compressed by the first inflatable portion 206a. Alternatively, in order to make the distribution of the compression force uniform within the compression region, the plurality of inflation restricting portions 50 are preferably disposed in a distributed manner in the plan view viewed along the thickness direction T1.

As shown in FIG. 9, each inflation restricting portion 50 according to the present embodiment includes a straight line portion extending in a straight line shape in the plan view viewed along the thickness direction T1. More specifically, the inflation restricting portion 50 according to the present embodiment is implemented by only the straight line portion extending in a straight line shape in the plan view viewed along the thickness direction T1. With such a configuration, the first inflatable portion 206a in the inflated form can be relatively easily curved by bending of the straight line portion of the inflation restricting portion 50. Therefore, followability of the first inflatable portion 206a to the biological surface can be further improved. As a result, the distribution of the compression force within the compression region of the first inflatable portion 206a can be made more uniform.

Similarly to the first inflatable portion 6a according to the first embodiment, the first inflatable portion 206a according to the present embodiment is inflated while pivoting. Therefore, as in the present embodiment, it is preferable that the straight line portion of the inflation restricting portion 50 extends in a direction (a left-right direction in FIG. 9) along a pivot central axis of the first inflatable portion 206a. In this way, the first inflatable portion 206a that compresses the biological surface while pivoting about the pivot central axis is relatively easily curved along the biological surface by bending the straight line portion of the inflation restricting portion 50.

As in the present embodiment, a plurality of (two in the present embodiment) straight line portions of the inflation restricting portion 50 each extending in the direction along the pivot central axis of the first inflatable portion 206a are preferably provided at different positions in a radial direction (an up-down direction in FIG. 9) when a virtual circle around the pivot central axis of the first inflatable portion 206a is assumed. In this way, the first inflatable portion 206a that compresses the biological surface while pivoting about the pivot central axis is relatively easily curved to follow the biological surface by bending the plurality of straight line portions of the inflation restricting portion 50.

Figure 11:
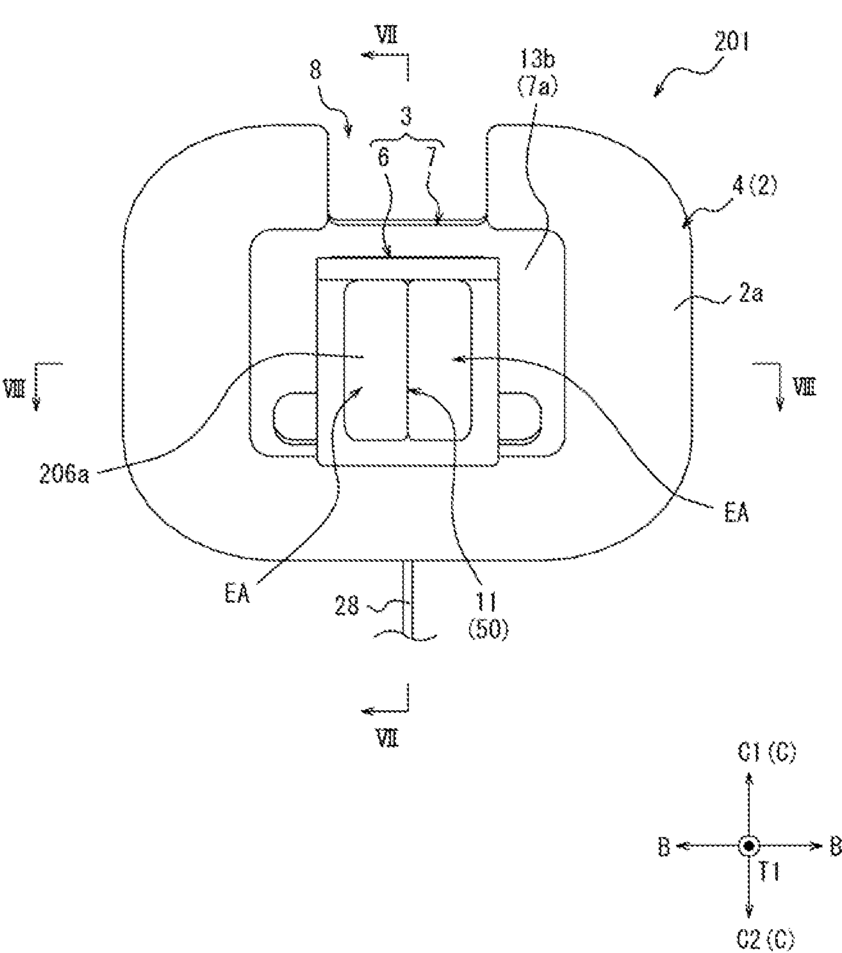
FIG. 11 is a plan view of a compression device including a first inflatable portion as a modification of the first inflatable portion according to the third embodiment viewed along a thickness direction of the first inflatable portion in an inflated form.
Figure 12A:
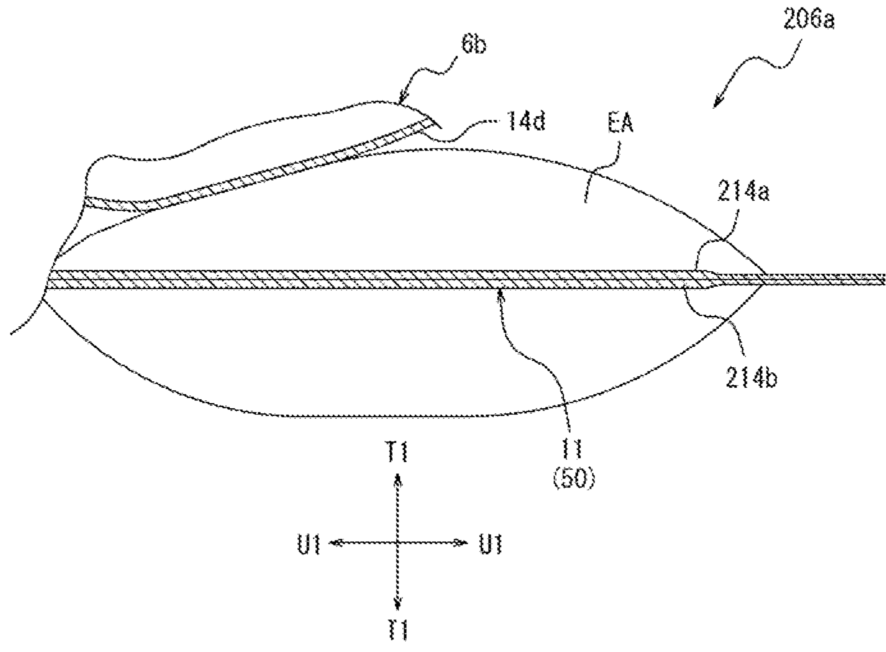
FIG. 12A is a cross-sectional view of the first inflatable portion taken along a line VII-VII in FIG. 11.
Figure 12B:
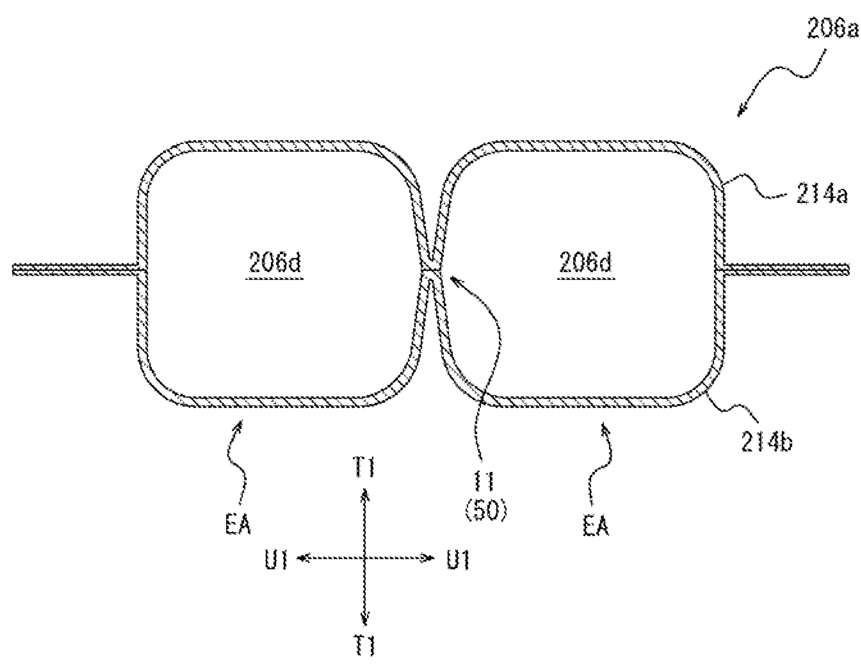
FIG. 12B is a cross-sectional view of the first inflatable portion taken along a line VIII-VIII in FIG. 11.
Figure 13:
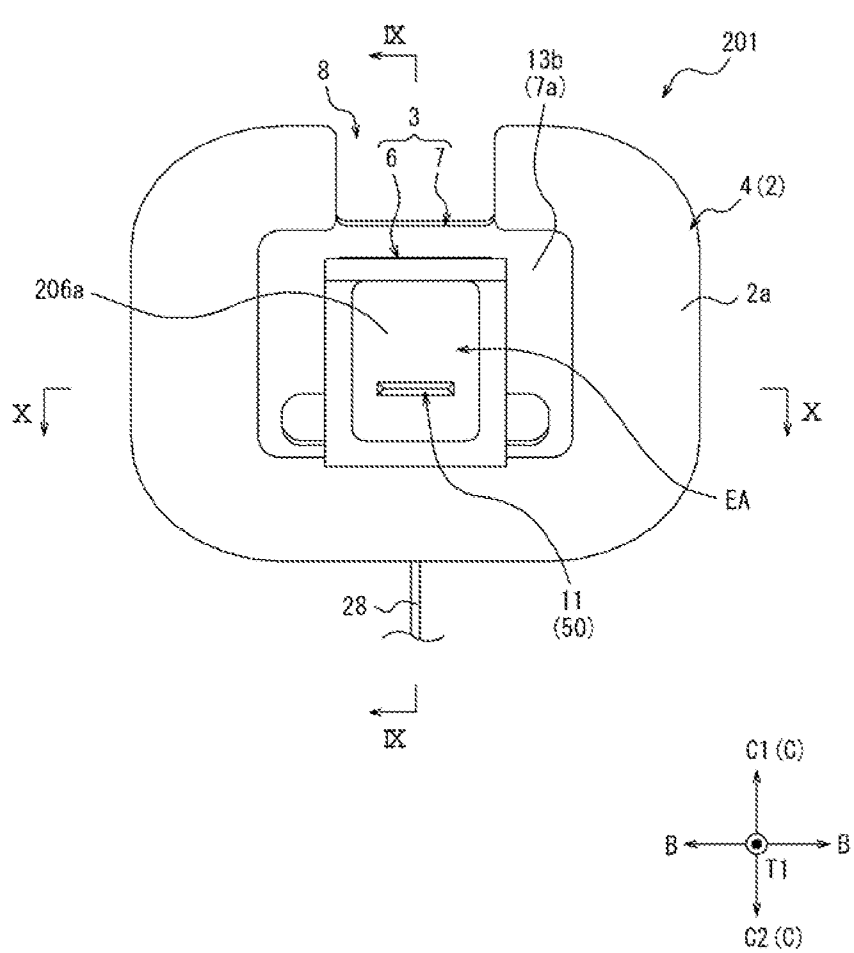
FIG. 13 is a plan view of a compression device including a first inflatable portion as another modification of the first inflatable portion according to the third embodiment viewed along a thickness direction of the first inflatable portion in an inflated form.
Figure 14A:
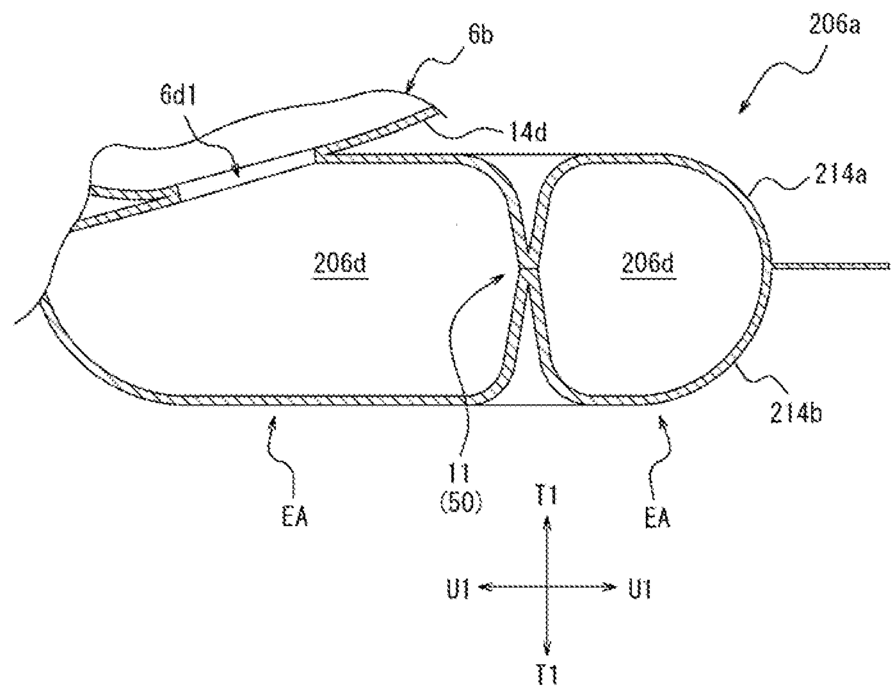
FIG. 14A is a cross-sectional view of the first inflatable portion taken along a line IX-IX in FIG. 13.
Figure 14B:
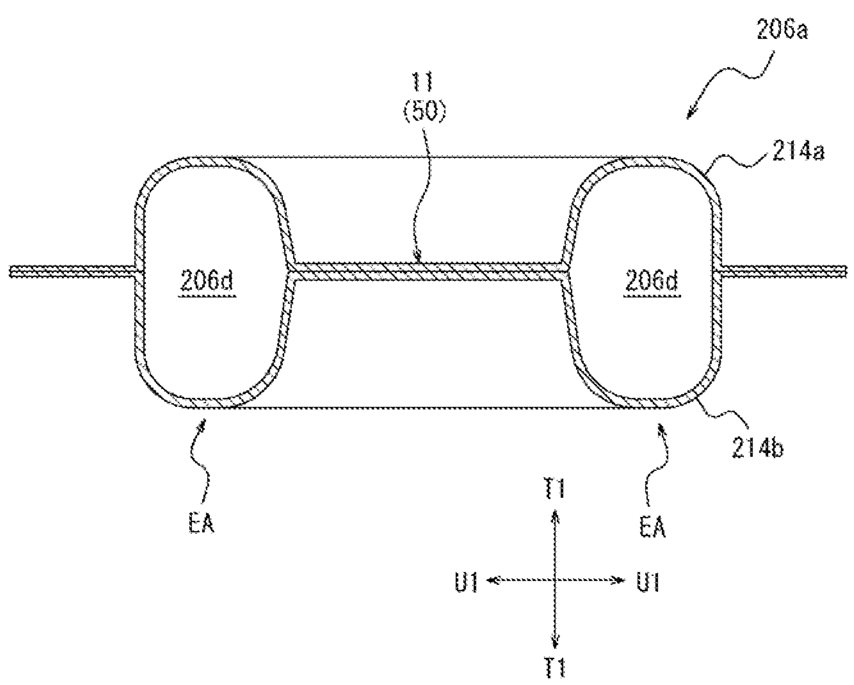
FIG. 14B is a cross-sectional view of the first inflatable portion taken along a line X-X in FIG. 13.

Alternatively, an extending direction, a position, and the number of the straight line portions of the inflation restricting portion 50 in the plan view viewed along the thickness direction T1 are not limited to the extending direction, the position, and the number of the straight line portions according to the present embodiment. For example, as shown in FIGS. 11, 12A, and 12B, the extending direction of the straight line portions of the inflation restricting portion 50 may be a direction along the radial direction (the up-down direction in FIG. 11) when the virtual circle around the pivot central axis of the first inflatable portion 206a is assumed. FIGS. 11, 12A, and 12B are diagrams showing a modification of the first inflatable portion 206a. FIG. 11 is a diagram showing a case where the first inflatable portion 206a of the compression device 201 is in the inflated form. FIG. 11 is a plan view of the first inflatable portion 206a viewed along the thickness direction T1. FIG. 12A is a cross-sectional view of the first inflatable portion 206a taken along a line VII-VII in FIG. 11. FIG. 12B is a cross-sectional view of the first inflatable portion 206a taken along a line VIII-VIII in FIG. 11. The extending direction of the straight line portions of the inflation restricting portion 50 may be appropriately determined according to the shape of the biological surface to be compressed by the first inflatable portion 206a.

In the modification shown in FIGS. 11, 12A, and 12B, two accommodation spaces 206d are separated by the inflation restricting portion 50. That is, the inflation restricting portion 50 may be configured to divide the two inflation regions EA adjacent to each other on both sides in the plan view viewed along the thickness direction T1 into separate accommodation spaces 206d that do not communicate with each other.

Further, the number of straight line portions of the inflation restricting portion 50 may be, for example, only one, as shown in FIGS. 11, 12A and 12B. The position of the straight line portions of the inflation restricting portion 50 is not particularly limited. As shown in FIG. 9, the straight line portion of the inflation restricting portion 50 may not be provided at the position including the center position of the accommodation spaces 206d in the plan view viewed along the thickness direction T1. As shown in FIG. 11, the straight line portion of the inflation restricting portion 50 may be provided at the position including the center position of the accommodation spaces 206d in the plan view viewed along the thickness direction T1. Further, as in the first inflatable portion 206a according to another modification shown in FIGS. 13, 14A, and 14B, straight line portions of the inflation restricting portion 50 may be disposed to be unevenly distributed in the plan view viewed along the thickness direction T1. As described above, the position and the number of the straight line portions of the inflation restricting portion 50 may be appropriately determined according to the shape of the biological surface to be compressed by the first inflatable portion 206a.

As in the first embodiment, each of the inflation restricting portions 50 is implemented by the sheet joint portion 11. Each of the inflation restricting portions 50 is not limited to the configuration of the sheet joint portion 11 formed by joining the sheet-shaped members 214a and 214b by heat sealing or the like, as long as the inflation in the thickness direction T1 is restricted as compared with the inflation region EA located around the inflation restricting portion 50 in the plan view viewed along the thickness direction T1. However, as described above, by constituting the inflation restricting portion 50 by the sheet joint portion 11, the inflation restricting portion 50 can be rather easily formed.

Finally, an example of a living body compression method executed by the compression device 1 according to the first embodiment, the compression device 101 according to the second embodiment, and the compression device 201 according to the third embodiment described above will be described. Here, for convenience of description, the living body compressing method is described using the compression device 1 according to the first embodiment, but the same applies to the compression device 101 according to the second embodiment and the compression device 201 according to the third embodiment.

Figure 15A:
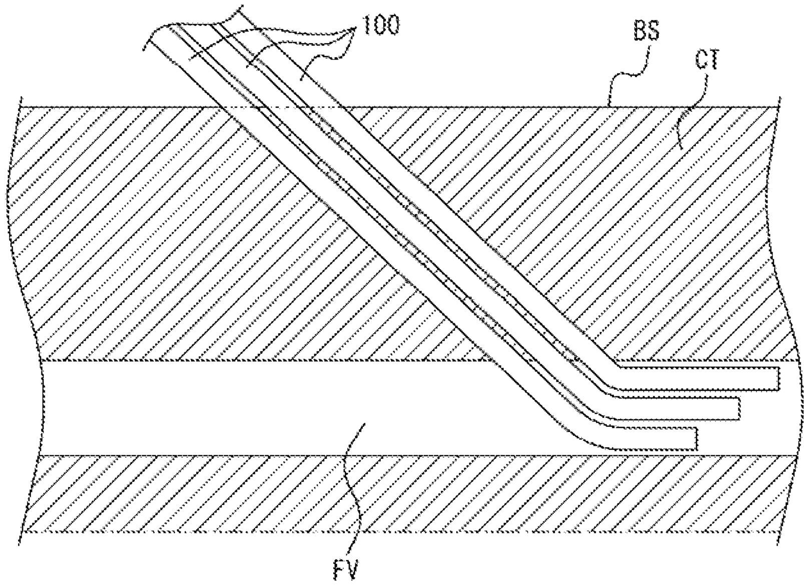
FIG. 15A is a diagram showing a state in which a medical insertion member is inserted into a femoral vein from a biological surface through a connective tissue.
Figure 15B:
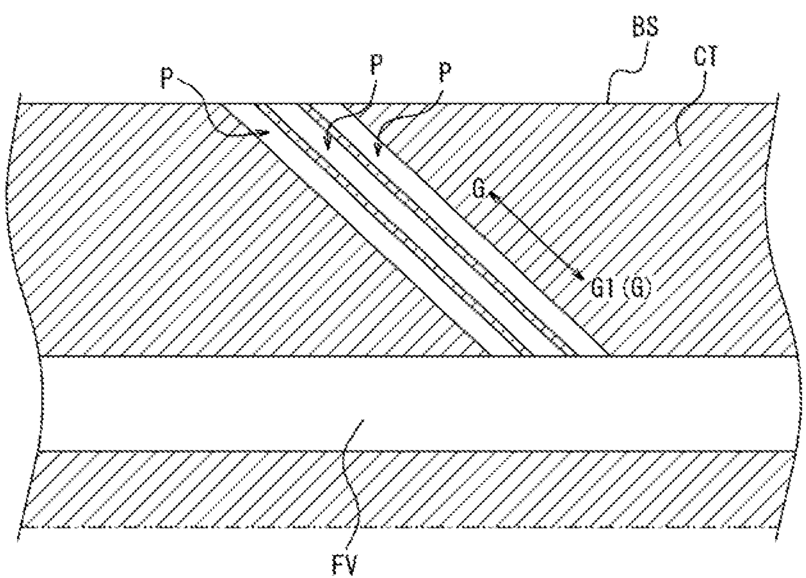
FIG. 15B is a diagram showing a state after the medical insertion member is removed from the state shown in FIG. 15A.

By compressing the biological surface BS with the compression device 1, a perforation leading from the biological surface to a vein can be narrowed or obstructed without obstructing the vein. The perforation is formed by removing a sheath as a medical insertion member 100 (see FIGS. 15A and 17) in a state of being inserted into a vein such as a femoral vein from the biological surface BS through a connective tissue. By the compression device 1, bleeding can be stopped after the sheath as the medical insertion member 100 is removed. First, the perforation formed after the medical insertion member 100 is removed will be described with reference to FIGS. 15A and 15B. FIG. 15A shows a state in which the sheath as the medical insertion member 100 is inserted into a femoral vein FV from the biological surface BS through a connective tissue CT. FIG. 15A shows three sheaths as the medical insertion members 100, and the number of sheaths may be, for example, two or less, or may be four or more. FIG. 15B shows a state after the sheaths as the medical insertion members 100 are removed from the state shown in FIG. 15A. As shown in FIG. 15B, when the sheaths as the medical insertion members 100 are removed, the perforations P are formed between the biological surface BS and the femoral vein FV. By using the compression device 1, the perforations P can be narrowed or obstructed without obstructing the femoral vein FV. Therefore, even when bleeding from a vein located at a deep position from the biological surface is stopped, bleeding can be stopped relatively efficiently without narrowing or obstructing the vein itself.

As described above, in a case of stopping the bleeding from the vein, the bleeding can be stopped by narrowing or obstructing the perforations P (see FIG. 15B). On the other hand, for example, in a case of stopping bleeding from a femoral artery, even when only the perforations are obstructed, the blood leaks and spreads in the connective tissue CT (see FIGS. 15A and 15B), and thus the bleeding cannot be stopped. In a case of stopping the bleeding from the femoral artery, it is necessary to take a large measure, such as a method for strongly compressing the artery itself until the artery is narrowed or obstructed, or a method for obstructing a hole of an artery wall.

Therefore, in a case of stopping the bleeding from the vein using the compression device 1, it is preferable to compress the biological surface BS to a position at which a compression depth from the biological surface BS can be, for example, 5 mm to 20 mm. By setting the compression depth within the above-mentioned range, it is rather easy to implement the compression state in which the perforations P (see FIG. 15B) are narrowed or obstructed without obstructing the vein. The compression depth can be, for example, preferably 5 mm to 15 mm, and more preferably 8 mm to 12 mm.

Further, in a case of stopping the bleeding from the vein using the compression device 1, it is preferable to compress the biological surface BS, for example, at 10 g/cm$^2$ to 600 g/cm$^2$ from the biological surface BS. Compression pressure is pressure after the sheath as the medical insertion member 100 is removed. By setting the compression pressure in the above-mentioned range, it is relatively easy to implement the compression state in which the perforations P (see FIG. 15B) are narrowed or obstructed without obstructing the vein. The compression pressure can be, for example, preferably 50 g/cm$^2$ to 400 g/cm$^2$, and more preferably 100 g/cm$^2$ to 300 g/cm$^2$.

It is preferable to compress the biological surface BS along a direction orthogonal to an extending direction of the perforations P (see FIG. 15B). The expression "compressing the biological surface BS along a direction orthogonal to an extending direction of the perforations" means not only compressing only in the direction orthogonal to the extending direction of the perforations but also compressing in a direction inclined at an angle equal to or less than a predetermined angle (for example, 30 degrees or less) with respect to the direction orthogonal to the extending direction of the perforations. The compression device 1 can compress the biological surface BS along the direction orthogonal to the extending direction of the perforations P (see FIG. 15B).

Figure 16:
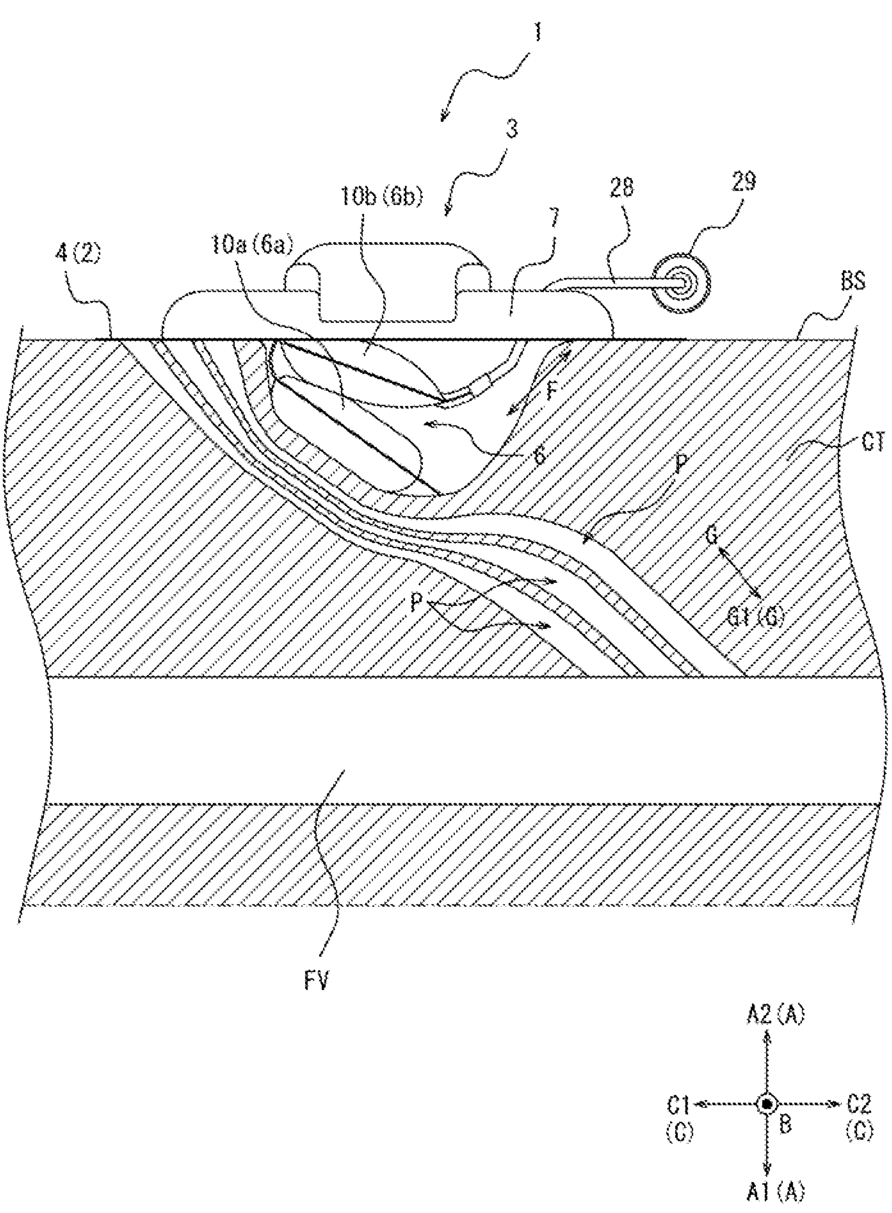
FIG. 16 is a diagram showing a state in which perforations shown in FIG. 15B are narrowed or obstructed by the compression device shown in FIG. 1.

Specifically, as described above, the first inflatable portion 6*a* and the second inflatable portion 6*b* of the compression device 1 can be inflated toward the direction inclined with respect to the thickness direction A. Accordingly, the biological surface can be compressed along the direction orthogonal to the extending direction of the perforations P (see FIG. 15B). Specifically, as shown in FIGS. 15A and 15B, the sheath as the medical insertion member 100 is inserted not in a direction orthogonal to the biological surface BS (the same direction as the thickness direction A) but in a direction inclined to one side with respect to the direction orthogonal to the biological surface BS. Therefore, as shown in FIG. 15B, the extending direction of the perforations P is also inclined with respect to the direction orthogonal to the biological surface BS. Therefore, when the first inflatable portion 6*a* and the second inflatable portion 6*b* can be inflated in a direction inclined to a side opposite to the extending direction of the perforations P (hereinafter, may be referred to as an "inclination direction F") with respect to the thickness direction A which is the direction orthogonal to the biological surface BS, the biological surface BS is rather easily compressed along the direction orthogonal to the extending direction of the perforations P. Accordingly, it can be easy to implement the compression device 1 that narrows or obstructs the perforations P without obstructing the vein such as the femoral vein FV in FIGS. 15A and 15B. FIG. 16 is a diagram showing the state in which the perforations P shown in FIG. 15B are narrowed or obstructed by the compression device 1. As shown in FIG. 16, the compression device 1 rather easily narrows or obstructs the perforations P without further obstructing the vein such as the femoral vein FV.

As described above, in a case of stopping the bleeding from the vein using the compression device 1, the bleeding can be stopped by narrowing or obstructing the perforations P (see FIG. 15B) without obstructing the vein such as the femoral vein FV. In particular, by implementing the living body compression method using the compression device 1, it is possible to stop the bleeding by a method without compression by a hand of the healthcare worker or using a large-scale hemostasis device.

Compression of Compression Device 1 on Biological Surface

As shown in FIG. 16, in the compression device 1, the first inflatable portion 6*a* of the compression member 3 can compress the biological surface BS toward the inclination direction F inclined with respect to a vertical direction perpendicular to the biological surface in a state in which the adhesion body 102 is adhered to the living body. Hereinafter, the thickness direction A and the up-down direction in FIG. 16 is referred to as the "vertical direction", which is the same direction as the thickness direction A and the up-down direction in FIG. 16. Accordingly, as shown in FIG. 16, the perforations P can be easily narrowed or obstructed without obstructing the vein such as the femoral vein FV.

Figure 17:
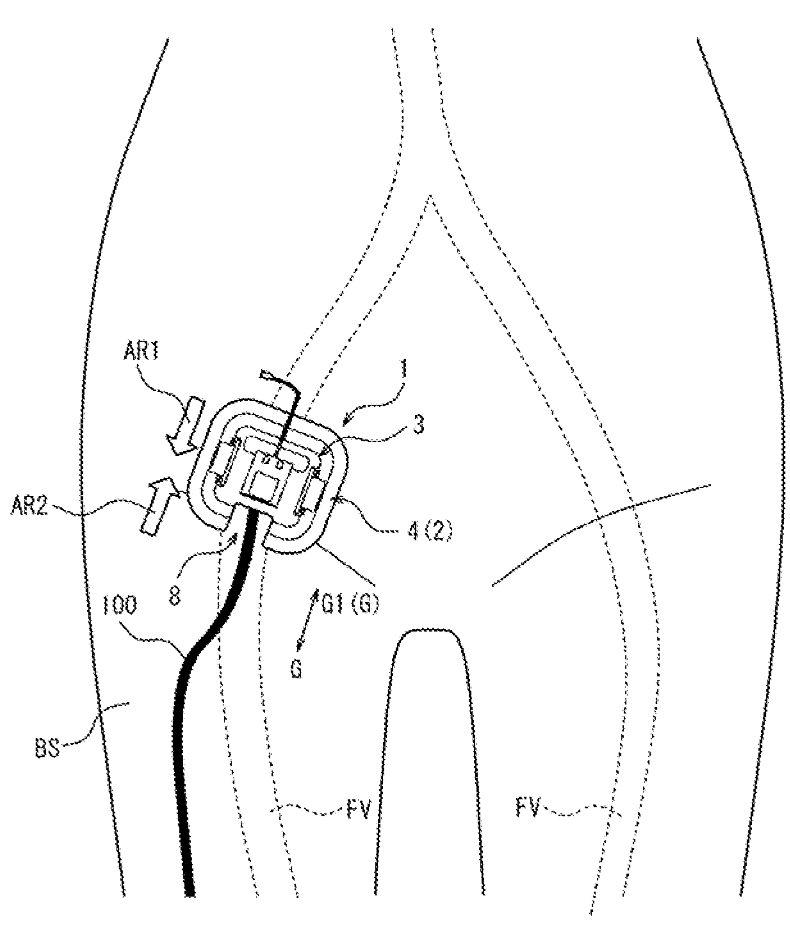
FIG. 17 is a front view of the state shown in FIG. 16 as viewed from a biological surface side.

FIG. 17 is a front view of the state shown in FIG. 16 as viewed from a biological surface BS side. In other words, FIG. 17 shows a front view of the biological surface BS at a position compressed by the compression device 1. Here, the expression "a front view of the biological surface at a position compressed by the compression device" means a state in which a portion of the biological surface to be compressed by the compression device is viewed from a direction perpendicular to the portion before the compression. FIG. 17 shows a front view of an inguinal region. In the front view shown in FIG. 17, a direction in which the biological surface BS is compressed (see a white arrow "AR1" in FIG. 17) is opposite to an insertion direction G1 (see a white arrow "AR2" in FIG. 17) of the sheath from the biological surface BS toward the vein in an extending direction G of the perforations P. That is, the direction in which the compression device 1 compresses the biological surface BS is opposite to the insertion direction G1 of the sheath in the front view shown in FIG. 17. Accordingly, the perforations P (see FIGS. 15B and 16) can be easily narrowed or obstructed without obstructing the vein such as the femoral vein FV.

In other words, as shown in FIG. 16, the extending direction G of the perforations P is inclined with respect to the biological surface BS and is also inclined with respect to the vertical direction (the up-down direction in FIG. 16) perpendicular to the biological surface BS. In addition, as shown in FIG. 16, a compression direction of the compression device 1 on the biological surface BS is also inclined with respect to the biological surface BS and also inclined with respect to the vertical direction (the up-down direction in FIG. 16) perpendicular to the biological surface BS. Further, as shown in FIG. 16, the extending direction G of the perforations P is inclined to a side opposite to the inclination direction F as the compression direction of the compression device 1 on the biological surface with respect to the vertical direction (the up-down direction in FIG. 16). That is, the compression of the compression device 1 on the biological surface is executed such that the compression direction intersects with the extending direction G of the perforations P. Accordingly, the perforations P can be efficiently narrowed or obstructed.

The compression device according to the present disclosure is not limited to the specific configurations shown in the embodiments and modifications, and various modifications, changes, and combinations may be made without departing from the description of the claims. It is expressly intended that all such changes, modifications and equivalents which fall within the scope of the claims are embraced by the claims. For example, the inflation restricting portion 50 may extend in a curved shape in the plan view viewed along the thickness direction T1. The first inflatable portion may include, for example, both the point-shaped inflation restricting portion 50 (see FIGS. 2B and 7) in the plan view viewed along the thickness direction T1 and the linear inflation restricting portion 50 (see FIGS. 9, 11, and 13) extending in a curved shape or extending in a straight line shape in the plan view viewed along the thickness direction T1. Further, the first inflatable portion may include, for example, linear inflation restricting portions 50 intersecting each other in the plan view viewed along the thickness direction T1. As an example, the first inflatable portion may include both the inflation restricting portion 50 extending in the straight line shape shown in FIG. 9 and the inflation restricting portion 50 extending in the straight line shape shown in FIG. 11.

The detailed description above describes embodiments of a compression device. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A compression device, comprising:

an adhesion surface configured to be adhered to a biological surface; an inflatable portion configured to compress the biological surface; the inflatable portion defining an accommodation space configured to accommodate a fluid, the inflatable portion being configured to be inflated in a thickness direction from a flat deflated form and to be changed to an inflated form by supplying the fluid to the accommodation space;

wherein the inflatable portion is provided with an inflation restricting portion, the inflation restricting portion being provided at a position sandwiched or surrounded by inflation regions configured to be inflatable in the thickness direction in a plan view viewed along the thickness direction, and in which inflation in the thickness direction is restricted by the inflation regions;

wherein the inflatable portion defines the accommodation space between two members facing each other in the thickness direction;

the inflation restricting portion is formed by joining the two members in the thickness direction;

the two members are two sheet-shaped members that are stacked; and the accommodation space is defined by a central portion where the two sheet-shaped members are not joined to each other and that is surrounded by peripheral portions of the two sheet-shaped members that are joined to each other.

2. The compression device according to claim 1, wherein the inflation restricting portion is provided at a position including a center position of the accommodation space in the plan view viewed along the thickness direction.

3. The compression device according to claim 1, further comprising:

a plurality of the inflation restricting portions are provided at positions separated from each other in the plan view viewed along the thickness direction.

4. The compression device according to claim 1, wherein the inflation restricting portion includes a straight line portion extending in a straight line shape in the plan view viewed along the thickness direction.

5. The compression device according to claim 1, further comprising:

an adhesion body having the adhesion surface;

a compression member attached to the adhesion body and including the inflatable portion;

the compression member includes an inflatable body including the inflatable portion and a support body fixed to the adhesion body and configured to support the inflatable body, and when the inflatable portion is a first inflatable portion;

the inflatable body includes the first inflatable portion and a second inflatable portion configured to press the first inflatable portion toward the biological surface by being inflated in the thickness direction from the flat deflated form and being changed to the inflated form in a state of being sandwiched between the support body and the first inflatable portion; and the second inflatable portion is not provided with the inflation restricting portion.

6. The compression device according to claim 5, wherein the inflatable body includes an extending portion extending from the first inflatable portion and the second inflatable portion;

the support body defines a through-hole penetrating from one side to the other side in a direction orthogonal to the adhesion surface; and the inflatable body is attached to the support body in a state in which the extending portion extends through the through-hole of the support body from the one side where the first inflatable portion and the second inflatable portion are located with the support body interposed between the first inflatable portion and the second inflatable portion to the other side and is wound around the support body.

7. A compression device, comprising:

an adhesion surface configured to be adhered to a biological surface;

an inflatable portion configured to compress the biological surface;

the inflatable portion defining an accommodation space configured to accommodate a fluid, the inflatable portion being configured to be inflated from a flat deflated form and to be changed to an inflated form by supplying the fluid to the accommodation space;

an adhesion body having the adhesion surface;

a compression member attached to the adhesion body and including the inflatable portion;

wherein the inflatable portion is provided with an inflation restricting portion, the inflation restricting portion configured to restrict inflation of the inflatable portion;

wherein the compression member includes an inflatable body including the inflatable portion and a support body fixed to the adhesion body and configured to support the inflatable body, and when the inflatable portion is a first inflatable portion;

wherein the inflatable body includes the first inflatable portion and a second inflatable portion configured to press the first inflatable portion toward a biological surface by being inflated from the flat deflated form and being changed to the inflated form in a state of being sandwiched between the support body and the first inflatable portion; and wherein the second inflatable portion is not provided with the inflation restricting portion.

8. The compression device according to claim 7, wherein the inflation restricting portion is between inflation regions of the inflatable portion.

9. The compression device according to claim 7, wherein the inflation restricting portion surrounds inflation regions of the inflatable portion.

10. The compression device according to claim 7, wherein the inflation restricting portion is provided at a center position of the accommodation space.

11. The compression device according to claim 7, wherein the inflation restricting portion comprises a plurality of inflation restricting portions provided at positions separated from each other.

12. The compression device according to claim 7, wherein the inflation restricting portion includes a straight line portion extending in a straight line shape.

13. The compression device according to claim 7, wherein the inflatable portion defines the accommodation space between two members facing each other, and the inflation restricting portion is formed by joining the two members.

14. The compression device according to claim 13, wherein the two members are two sheet-shaped members that are stacked, and the accommodation space is defined by a central portion where the two sheet-shaped members are not joined to each other and are surrounded by peripheral portions of the two sheet-shaped members that are joined to each other.

15. The compression device according to claim 7, wherein the inflatable body includes an extending portion extending from the first inflatable portion and the second inflatable portion;

the support body defines a through-hole penetrating from one side to the other side in a direction orthogonal to the adhesion surface; and the inflatable body is attached to the support body in a state in which the extending portion extends through the through-hole of the support body from the one side where the first inflatable portion and the second inflatable portion are located with the support body interposed between the first inflatable portion and the second inflatable portion to the other side and is wound around the support body.

* * * * *